(12) United States Patent
Rush et al.

(10) Patent No.: US 8,047,811 B2
(45) Date of Patent: Nov. 1, 2011

(54) VARIABLE VOLUME, SHAPE MEMORY ACTUATED INSULIN DISPENSING PUMP

(75) Inventors: Benjamin M. Rush, Oakland, CA (US); Christopher V. Reggiardo, Castro Valley, CA (US); Arthur E. Anderson, III, Sunnyvale, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/345,545

(22) Filed: Dec. 29, 2008

(65) Prior Publication Data

US 2009/0105647 A1 Apr. 23, 2009

Related U.S. Application Data

(60) Division of application No. 11/106,155, filed on Apr. 13, 2005, which is a continuation-in-part of application No. 10/683,659, filed on Oct. 9, 2003, now Pat. No. 6,916,159.

(60) Provisional application No. 60/424,613, filed on Nov. 6, 2002, provisional application No. 60/417,464, filed on Oct. 9, 2002.

(51) Int. Cl.
*F01B 23/08* (2006.01)
(52) U.S. Cl. .................... 417/321; 417/410.1
(58) Field of Classification Search ............ 417/53, 417/321, 415, 12, 44.1, 199.2, 200, 326, 417/410.1; 310/306, 307; 60/527, 528; 318/117; 222/52, 63
See application file for complete search history.

(56) References Cited

U.S. PATENT DOCUMENTS

| | | | | |
|---|---|---|---|---|
| 2,508,253 | A | * | 5/1950 | Haggardt ................ 417/254 |
| 2,915,579 | A | | 12/1959 | Mendelsohn |
| 3,374,337 | A | * | 3/1968 | Burley ................ 219/501 |
| 3,510,747 | A | | 5/1970 | Petrides |
| 3,541,892 | A | | 11/1970 | Kubinek et al. |
| 3,606,592 | A | | 9/1971 | Madurski et al. |
| 3,750,687 | A | | 8/1973 | Williams |
| 3,843,455 | A | | 10/1974 | Bier |
| 3,923,060 | A | | 12/1975 | Elinwood |

(Continued)

FOREIGN PATENT DOCUMENTS

EP  0455455  11/1991

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Devon C Kramer
*Assistant Examiner* — Dnyanesh Kasture
(74) *Attorney, Agent, or Firm* — Jackson & Co., LLP

(57) ABSTRACT

A portable pumping system provides insulin or other drugs to a user. A shape memory element is used to actuate the pump and an intelligent system controls the actuator in order to minimize stresses within the system and provide accurate and reliable dosage delivery. The control system utilizes various types of feedback to monitor and optimize the position of the pumping mechanisms. Physical design aspects also minimize stress and the combination of the physical design aspects and the intelligent operation of the system results in a lightweight and cost effective pump that may be used in a disposable fashion if desired.

17 Claims, 16 Drawing Sheets

U.S. PATENT DOCUMENTS

| | | |
|---|---|---|
| 3,930,493 A | 1/1976 | Williamson |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Elinwood |
| 4,193,397 A | 3/1980 | Tucker et al. |
| 4,268,173 A | 5/1981 | Barnard et al. |
| 4,288,793 A | 9/1981 | Lotscher |
| 4,309,156 A * | 1/1982 | Gonner et al. ............. 417/403 |
| 4,362,052 A | 12/1982 | Heath et al. |
| 4,401,122 A | 8/1983 | Clark, Jr. |
| 4,439,197 A | 3/1984 | Honda et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A * | 6/1985 | Morgan et al. ............. 337/140 |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A * | 3/1989 | Palmer ............. 60/527 |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Bush et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A * | 5/1993 | Coffee ............. 251/11 |
| 5,211,626 A | 5/1993 | Frank et al. |
| 5,223,822 A | 6/1993 | Stommes et al. |
| 5,262,305 A | 11/1993 | Heller et al. |
| 5,267,026 A | 11/1993 | Kawahara et al. |
| 5,278,997 A | 1/1994 | Martin |
| 5,284,423 A * | 2/1994 | Holdsworth et al. ............ 417/28 |
| 5,291,614 A | 3/1994 | Baker et al. |
| 5,291,887 A | 3/1994 | Stanley et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A * | 4/1997 | Lee ............. 417/321 |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,919,167 A | 7/1999 | Mulhauser |
| 5,923,512 A | 7/1999 | Brownlow et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |
| 5,965,380 A | 10/1999 | Heller et al. |
| 5,968,011 A | 10/1999 | Larsen et al. |
| 5,971,922 A | 10/1999 | Arita et al. |

| | | |
|---|---|---|
| 5,994,878 A | 11/1999 | Ostergaard et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |
| 6,086,575 A | 7/2000 | Mejslov |
| 6,091,975 A | 7/2000 | Daddona et al. |
| 6,093,156 A | 7/2000 | Cunningham et al. |
| 6,093,172 A | 7/2000 | Funderburk et al. |
| 6,121,009 A | 9/2000 | Heller et al. |
| 6,129,823 A | 10/2000 | Hughes et al. |
| 6,132,371 A | 10/2000 | Dempsey et al. |
| 6,142,939 A | 11/2000 | Eppstein et al. |
| 6,144,303 A | 11/2000 | Federman |
| 6,144,869 A | 11/2000 | Berner et al. |
| 6,144,922 A | 11/2000 | Douglas et al. |
| 6,147,342 A | 11/2000 | Kucher |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,201,980 B1 | 3/2001 | Darrow et al. |
| 6,203,288 B1 | 3/2001 | Kottke |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,215,206 B1 * | 4/2001 | Chitayat .................... 310/12.14 |
| 6,222,514 B1 | 4/2001 | DeLuca |
| 6,228,100 B1 | 5/2001 | Schraga |
| 6,232,370 B1 | 5/2001 | Kubota et al. |
| 6,233,471 B1 | 5/2001 | Berner et al. |
| 6,233,539 B1 | 5/2001 | Brown |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,283,951 B1 | 9/2001 | Flaherty et al. |
| 6,284,478 B1 | 9/2001 | Heller et al. |
| 6,288,653 B1 | 9/2001 | Shih |
| 6,293,925 B1 | 9/2001 | Safabash et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,379,301 B1 | 4/2002 | Worthington et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,484,045 B1 | 11/2002 | Holker et al. |
| 6,484,046 B1 | 11/2002 | Say et al. |
| 6,485,138 B1 | 11/2002 | Kubota et al. |
| 6,485,461 B1 | 11/2002 | Mason et al. |
| 6,485,465 B2 | 11/2002 | Morberg et al. |
| 6,492,180 B2 | 12/2002 | Brown et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |

| Patent | Date | Inventor |
|---|---|---|
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,980 B2 | 12/2003 | Morberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B1 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 * | 8/2004 | Lilie et al. ..................... 417/63 |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |

| | | | |
|---|---|---|---|
| 7,108,778 B2 | 9/2006 | Simpson et al. | |
| 7,110,803 B2 | 9/2006 | Shults et al. | |
| 7,114,502 B2 | 10/2006 | Schulman et al. | |
| 7,123,206 B2 | 10/2006 | Hess et al. | |
| 7,133,710 B2 | 11/2006 | Acosta et al. | |
| 7,134,999 B2 | 11/2006 | Brauker et al. | |
| 7,136,689 B2 | 11/2006 | Shults et al. | |
| 7,136,704 B2 | 11/2006 | Schulman | |
| 7,137,964 B2 | 11/2006 | Flaherty | |
| 7,144,384 B2 | 12/2006 | Gorman et al. | |
| 7,149,581 B2 | 12/2006 | Goedeke | |
| 7,153,212 B1 | 12/2006 | Karten et al. | |
| 7,154,398 B2 | 12/2006 | Chen et al. | |
| 7,163,511 B2 | 1/2007 | Conn et al. | |
| 7,167,818 B2 | 1/2007 | Brown | |
| 7,171,274 B2 | 1/2007 | Starkweather et al. | |
| 7,181,261 B2 | 2/2007 | Silver et al. | |
| 7,186,566 B2 | 3/2007 | Qian | |
| 7,186,791 B2 | 3/2007 | Bruno et al. | |
| 7,192,450 B2 | 3/2007 | Brauker et al. | |
| 7,193,521 B2 | 3/2007 | Morberg et al. | |
| 7,198,603 B2 | 4/2007 | Penner et al. | |
| 7,202,734 B1 | 4/2007 | Raab | |
| 7,205,409 B2 | 4/2007 | Pei et al. | |
| 7,208,119 B1 | 4/2007 | Kurtock et al. | |
| 7,211,048 B1 | 5/2007 | Najafi et al. | |
| 7,218,017 B1 | 5/2007 | Chitayat et al. | |
| 7,225,535 B2 | 6/2007 | Feldman et al. | |
| 7,226,278 B2 | 6/2007 | Nason et al. | |
| 7,226,442 B2 | 6/2007 | Sheppard, Jr. et al. | |
| 7,226,978 B2 | 6/2007 | Tapsak et al. | |
| 7,258,666 B2 | 8/2007 | Brown | |
| 7,266,400 B2 | 9/2007 | Fine et al. | |
| 7,276,029 B2 | 10/2007 | Goode, Jr. et al. | |
| 7,283,867 B2 | 10/2007 | Strother et al. | |
| 7,299,080 B2 | 11/2007 | Acosta et al. | |
| 7,303,549 B2 | 12/2007 | Flaherty et al. | |
| 7,310,544 B2 | 12/2007 | Brister et al. | |
| 7,323,091 B1 | 1/2008 | Gillette et al. | |
| 7,324,949 B2 | 1/2008 | Bristol et al. | |
| 7,343,188 B2 | 3/2008 | Sohrab | |
| 7,364,592 B2 | 4/2008 | Carr-Brendel et al. | |
| 7,366,556 B2 | 4/2008 | Brister et al. | |
| 7,371,247 B2 | 5/2008 | Boecker et al. | |
| 7,379,765 B2 | 5/2008 | Petisce et al. | |
| 7,424,318 B2 | 9/2008 | Brister et al. | |
| 7,436,511 B2 | 10/2008 | Ruchti et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,480,138 B2 | 1/2009 | Kogan et al. | |
| 7,494,465 B2 | 2/2009 | Brister et al. | |
| 7,497,827 B2 | 3/2009 | Brister et al. | |
| 7,510,526 B2 | 3/2009 | Merry et al. | |
| 7,519,408 B2 | 4/2009 | Rasdal et al. | |
| 7,583,190 B2 | 9/2009 | Reggiardo et al. | |
| 7,583,990 B2 | 9/2009 | Goode, Jr. et al. | |
| 7,591,801 B2 | 9/2009 | Brauker et al. | |
| 7,599,726 B2 | 10/2009 | Goode, Jr. et al. | |
| 7,602,310 B2 | 10/2009 | Mann et al. | |
| 7,613,491 B2 | 11/2009 | Boock et al. | |
| 7,615,007 B2 | 11/2009 | Shults et al. | |
| 7,620,437 B2 | 11/2009 | Reggiardo | |
| 7,632,228 B2 | 12/2009 | Brauker et al. | |
| 7,637,868 B2 | 12/2009 | Saint et al. | |
| 7,640,048 B2 | 12/2009 | Dobbles et al. | |
| 7,651,596 B2 | 1/2010 | Petisce et al. | |
| 7,654,956 B2 | 2/2010 | Brister et al. | |
| 7,657,297 B2 | 2/2010 | Simpson et al. | |
| 7,679,407 B2 | 3/2010 | Reggiardo | |
| 7,711,402 B2 | 5/2010 | Shults et al. | |
| 7,713,574 B2 | 5/2010 | Brister et al. | |
| 7,715,893 B2 | 5/2010 | Kamath et al. | |
| 7,727,181 B2 | 6/2010 | Rush et al. | |
| 7,753,873 B2 | 7/2010 | Rush | |
| 7,753,874 B2 | 7/2010 | Rush et al. | |
| 7,756,561 B2 | 7/2010 | Reggiardo et al. | |
| 7,766,864 B2 | 8/2010 | Rush et al. | |
| 7,850,621 B2 | 12/2010 | Briggs et al. | |
| 2001/0016682 A1 | 8/2001 | Berner et al. | |
| 2001/0016683 A1 | 8/2001 | Darrow et al. | |
| 2001/0016710 A1 | 8/2001 | Nason et al. | |
| 2001/0020124 A1 | 9/2001 | Tamada | |
| 2001/0023095 A1 | 9/2001 | Kopley et al. | |
| 2001/0024864 A1 | 9/2001 | Kopley et al. | |
| 2001/0029340 A1 | 10/2001 | Mault et al. | |
| 2001/0034502 A1 | 10/2001 | Moberg et al. | |
| 2001/0037060 A1 | 11/2001 | Thompson et al. | |
| 2001/0037069 A1 | 11/2001 | Carlson et al. | |
| 2001/0041830 A1 | 11/2001 | Varalli et al. | |
| 2001/0044581 A1 | 11/2001 | Mault | |
| 2001/0044588 A1 | 11/2001 | Mault | |
| 2001/0049470 A1 | 12/2001 | Mault et al. | |
| 2001/0053891 A1 | 12/2001 | Ackley | |
| 2001/0056255 A1 | 12/2001 | Kost et al. | |
| 2002/0002326 A1 | 1/2002 | Causey, III et al. | |
| 2002/0002328 A1 | 1/2002 | Tamada | |
| 2002/0004640 A1 | 1/2002 | Conn et al. | |
| 2002/0010414 A1 | 1/2002 | Coston et al. | |
| 2002/0019022 A1 | 2/2002 | Dunn et al. | |
| 2002/0019612 A1 | 2/2002 | Watanabe et al. | |
| 2002/0026937 A1 | 3/2002 | Mault | |
| 2002/0027164 A1 | 3/2002 | Mault et al. | |
| 2002/0028995 A1 | 3/2002 | Mault | |
| 2002/0032374 A1 | 3/2002 | Holker et al. | |
| 2002/0040208 A1 | 4/2002 | Flaherty et al. | |
| 2002/0042090 A1 | 4/2002 | Heller et al. | |
| 2002/0042561 A1 | 4/2002 | Schulman et al. | |
| 2002/0045808 A1 | 4/2002 | Ford et al. | |
| 2002/0047867 A1 | 4/2002 | Mault et al. | |
| 2002/0053637 A1 | 5/2002 | Conn et al. | |
| 2002/0062069 A1 | 5/2002 | Mault | |
| 2002/0068858 A1 | 6/2002 | Braig et al. | |
| 2002/0077765 A1 | 6/2002 | Mault | |
| 2002/0077766 A1 | 6/2002 | Mault | |
| 2002/0087056 A1 | 7/2002 | Aceti et al. | |
| 2002/0091312 A1 | 7/2002 | Berner et al. | |
| 2002/0091454 A1 | 7/2002 | Vasko | |
| 2002/0103425 A1 | 8/2002 | Mault | |
| 2002/0107433 A1 | 8/2002 | Mault | |
| 2002/0107476 A1 | 8/2002 | Mann et al. | |
| 2002/0109600 A1 | 8/2002 | Mault et al. | |
| 2002/0118090 A1 | 8/2002 | Park et al. | |
| 2002/0119711 A1 | 8/2002 | Van Antwerp et al. | |
| 2002/0124017 A1 | 9/2002 | Mault | |
| 2002/0133378 A1 | 9/2002 | Mault et al. | |
| 2002/0161286 A1 | 10/2002 | Gerber et al. | |
| 2002/0169394 A1 | 11/2002 | Eppstein et al. | |
| 2002/0169439 A1 | 11/2002 | Flaherty et al. | |
| 2002/0177764 A1 | 11/2002 | Sohrab | |
| 2002/0193679 A1 | 12/2002 | Malave et al. | |
| 2003/0009133 A1* | 1/2003 | Ramey .................. 604/155 |
| 2003/0023182 A1 | 1/2003 | Mault et al. | |
| 2003/0023317 A1 | 1/2003 | Brauker et al. | |
| 2003/0028089 A1 | 2/2003 | Galley et al. | |
| 2003/0028120 A1 | 2/2003 | Mault et al. | |
| 2003/0032868 A1 | 2/2003 | Graskov et al. | |
| 2003/0032874 A1 | 2/2003 | Rhodes et al. | |
| 2003/0040683 A1 | 2/2003 | Rule et al. | |
| 2003/0050546 A1 | 3/2003 | Desai et al. | |
| 2003/0050575 A1 | 3/2003 | Diermann et al. | |
| 2003/0055380 A1 | 3/2003 | Flaherty et al. | |
| 2003/0060692 A1 | 3/2003 | Ruchti et al. | |
| 2003/0060765 A1 | 3/2003 | Campbell et al. | |
| 2003/0065257 A1 | 4/2003 | Mault et al. | |
| 2003/0065273 A1 | 4/2003 | Mault et al. | |
| 2003/0065274 A1 | 4/2003 | Mault et al. | |
| 2003/0065275 A1 | 4/2003 | Mault et al. | |
| 2003/0065308 A1 | 4/2003 | Lebel et al. | |
| 2003/0078560 A1 | 4/2003 | Miller et al. | |
| 2003/0100040 A1 | 5/2003 | Bonnecaze et al. | |
| 2003/0100821 A1 | 5/2003 | Heller et al. | |
| 2003/0105407 A1 | 6/2003 | Pearce, Jr. et al. | |
| 2003/0107487 A1 | 6/2003 | Korman et al. | |
| 2003/0108976 A1 | 6/2003 | Braig et al. | |
| 2003/0118460 A1* | 6/2003 | Lilie et al. .................. 417/415 |
| 2003/0130616 A1 | 7/2003 | Steil et al. | |
| 2003/0134347 A1 | 7/2003 | Heller et al. | |

| | | | | | | |
|---|---|---|---|---|---|---|
| 2003/0135100 A1 | 7/2003 | Kim et al. | | 2004/0207054 A1 | 10/2004 | Brown et al. |
| 2003/0135333 A1 | 7/2003 | Aceti et al. | | 2004/0208780 A1 | 10/2004 | Faries, Jr. et al. |
| 2003/0153820 A1 | 8/2003 | Berner et al. | | 2004/0210184 A1 | 10/2004 | Kost et al. |
| 2003/0153821 A1 | 8/2003 | Berner et al. | | 2004/0225338 A1 | 11/2004 | Lebel et al. |
| 2003/0158472 A1 | 8/2003 | Sohrab | | 2004/0236200 A1 | 11/2004 | Say et al. |
| 2003/0158707 A1 | 8/2003 | Doi | | 2004/0248204 A1 | 12/2004 | Moerman |
| 2003/0167035 A1 | 9/2003 | Flaherty et al. | | 2004/0249250 A1 | 12/2004 | McGee et al. |
| 2003/0175806 A1 | 9/2003 | Rule et al. | | 2004/0249253 A1 | 12/2004 | Racchini et al. |
| 2003/0176933 A1 | 9/2003 | Lebel et al. | | 2004/0249254 A1 | 12/2004 | Racchini et al. |
| 2003/0181851 A1 | 9/2003 | Mann et al. | | 2004/0249999 A1 | 12/2004 | Connolly et al. |
| 2003/0181852 A1 | 9/2003 | Mann et al. | | 2004/0253736 A1 | 12/2004 | Stout et al. |
| 2003/0187338 A1 | 10/2003 | Say et al. | | 2004/0254429 A1 | 12/2004 | Yang |
| 2003/0187525 A1 | 10/2003 | Mann et al. | | 2004/0254434 A1 | 12/2004 | Goodnow et al. |
| 2003/0191376 A1 | 10/2003 | Samuels et al. | | 2004/0263354 A1 | 12/2004 | Mann et al. |
| 2003/0191431 A1 | 10/2003 | Mann et al. | | 2004/0264396 A1 | 12/2004 | Ginzburg et al. |
| 2003/0195403 A1 | 10/2003 | Berner et al. | | 2005/0003470 A1 | 1/2005 | Nelson et al. |
| 2003/0195462 A1 | 10/2003 | Mann et al. | | 2005/0009126 A1 | 1/2005 | Andrews et al. |
| 2003/0198558 A1 | 10/2003 | Nason et al. | | 2005/0010269 A1 | 1/2005 | Lebel et al. |
| 2003/0199825 A1 | 10/2003 | Flaherty | | 2005/0016276 A1 | 1/2005 | Guan et al. |
| 2003/0199837 A1 | 10/2003 | Vachon | | 2005/0027179 A1 | 2/2005 | Berner et al. |
| 2003/0208110 A1 | 11/2003 | Mault et al. | | 2005/0027180 A1 | 2/2005 | Goode, Jr. et al. |
| 2003/0208113 A1 | 11/2003 | Mault et al. | | 2005/0027181 A1 | 2/2005 | Goode, Jr. et al. |
| 2003/0208133 A1 | 11/2003 | Mault | | 2005/0027462 A1 | 2/2005 | Goode, Jr. et al. |
| 2003/0208154 A1 | 11/2003 | Close et al. | | 2005/0027463 A1 | 2/2005 | Goode, Jr. et al. |
| 2003/0208409 A1 | 11/2003 | Mault | | 2005/0031689 A1 | 2/2005 | Shults et al. |
| 2003/0212346 A1 | 11/2003 | Yuzhakov et al. | | 2005/0033132 A1 | 2/2005 | Shults et al. |
| 2003/0212364 A1 | 11/2003 | Mann et al. | | 2005/0038680 A1 | 2/2005 | McMahon |
| 2003/0212379 A1 | 11/2003 | Bylund et al. | | 2005/0043598 A1 | 2/2005 | Goode, Jr. et al. |
| 2003/0217966 A1 | 11/2003 | Tapsak et al. | | 2005/0043894 A1 | 2/2005 | Fernandez |
| 2003/0225360 A1 | 12/2003 | Eppstein et al. | | 2005/0045476 A1 | 3/2005 | Neel et al. |
| 2003/0225361 A1 | 12/2003 | Sabra | | 2005/0049473 A1 | 3/2005 | Desai et al. |
| 2003/0226695 A1 | 12/2003 | Mault | | 2005/0051580 A1 | 3/2005 | Ramey |
| 2003/0232370 A1 | 12/2003 | Trifiro | | 2005/0053365 A1 | 3/2005 | Adams et al. |
| 2003/0235817 A1 | 12/2003 | Bartkowiak et al. | | 2005/0054909 A1 | 3/2005 | Petisce et al. |
| 2004/0010207 A1 | 1/2004 | Flaherty et al. | | 2005/0059926 A1 | 3/2005 | Sage, Jr. et al. |
| 2004/0011671 A1 | 1/2004 | Shults et al. | | 2005/0065464 A1 | 3/2005 | Talbot et al. |
| 2004/0015131 A1 | 1/2004 | Flaherty et al. | | 2005/0090607 A1 | 4/2005 | Tapsak et al. |
| 2004/0018486 A1 | 1/2004 | Dunn et al. | | 2005/0090808 A1 | 4/2005 | Malave et al. |
| 2004/0019321 A1 | 1/2004 | Sage et al. | | 2005/0112169 A1 | 5/2005 | Brauker et al. |
| 2004/0027253 A1 | 2/2004 | Marsh et al. | | 2005/0113657 A1 | 5/2005 | Alarcon et al. |
| 2004/0030226 A1 | 2/2004 | Quy | | 2005/0113658 A1 | 5/2005 | Jacobson et al. |
| 2004/0039256 A1 | 2/2004 | Kawatahara et al. | | 2005/0118726 A1 | 6/2005 | Scultz et al. |
| 2004/0041749 A1 | 3/2004 | Dixon | | 2005/0121322 A1 | 6/2005 | Say et al. |
| 2004/0045879 A1 | 3/2004 | Shults et al. | | 2005/0124873 A1 | 6/2005 | Shults et al. |
| 2004/0054263 A1 | 3/2004 | Moerman et al. | | 2005/0137471 A1 | 6/2005 | Haar et al. |
| 2004/0059201 A1 | 3/2004 | Ginsberg | | 2005/0143635 A1 | 6/2005 | Kamath et al. |
| 2004/0059284 A1 | 3/2004 | Nash et al. | | 2005/0143636 A1 | 6/2005 | Zhang et al. |
| 2004/0064088 A1 | 4/2004 | Gorman et al. | | 2005/0148003 A1 | 7/2005 | Keith et al. |
| 2004/0064096 A1 | 4/2004 | Flaherty et al. | | 2005/0154271 A1 | 7/2005 | Rasdal et al. |
| 2004/0064133 A1 | 4/2004 | Miller et al. | | 2005/0161346 A1 | 7/2005 | Simpson et al. |
| 2004/0072357 A1 | 4/2004 | Stiene et al. | | 2005/0171503 A1 | 8/2005 | Van Den Berghe et al. |
| 2004/0073095 A1 | 4/2004 | Causey, III et al. | | 2005/0171512 A1 | 8/2005 | Flaherty |
| 2004/0085215 A1 | 5/2004 | Moberg et al. | | 2005/0171513 A1 | 8/2005 | Mann et al. |
| 2004/0096959 A1 | 5/2004 | Stiene et al. | | 2005/0173245 A1 | 8/2005 | Feldman et al. |
| 2004/0100376 A1 | 5/2004 | Lye et al. | | 2005/0176136 A1 | 8/2005 | Burd et al. |
| 2004/0106858 A1 | 6/2004 | Say et al. | | 2005/0177036 A1 | 8/2005 | Shults et al. |
| 2004/0106859 A1 | 6/2004 | Say et al. | | 2005/0181012 A1 | 8/2005 | Saint et al. |
| 2004/0106860 A1 | 6/2004 | Say et al. | | 2005/0182306 A1 | 8/2005 | Sloan |
| 2004/0108226 A1 | 6/2004 | Polychronakos et al. | | 2005/0182366 A1 | 8/2005 | Vogt et al. |
| 2004/0115067 A1 | 6/2004 | Rush et al. | | 2005/0182451 A1 | 8/2005 | Griffin et al. |
| 2004/0116866 A1 | 6/2004 | Gorman et al. | | 2005/0187720 A1 | 8/2005 | Goode, Jr. et al. |
| 2004/0122353 A1 | 6/2004 | Shahmirian et al. | | 2005/0192557 A1 | 9/2005 | Brauker et al. |
| 2004/0132220 A1 | 7/2004 | Fish | | 2005/0195930 A1 | 9/2005 | Spital et al. |
| 2004/0133092 A1 | 7/2004 | Kain | | 2005/0199494 A1 | 9/2005 | Say et al. |
| 2004/0152622 A1 | 8/2004 | Keith et al. | | 2005/0203360 A1 | 9/2005 | Brauker et al. |
| 2004/0153032 A1 | 8/2004 | Garribotto et al. | | 2005/0203461 A1 | 9/2005 | Flaherty et al. |
| 2004/0158137 A1 | 8/2004 | Eppstein et al. | | 2005/0214892 A1 | 9/2005 | Kovatchev et al. |
| 2004/0162473 A1 | 8/2004 | Sohrab | | 2005/0215871 A1 | 9/2005 | Feldman et al. |
| 2004/0164961 A1 | 8/2004 | Bal et al. | | 2005/0215872 A1 | 9/2005 | Berner et al. |
| 2004/0167383 A1 | 8/2004 | Kim et al. | | 2005/0218880 A1 | 10/2005 | Ioffe |
| 2004/0167801 A1 | 8/2004 | Say et al. | | 2005/0235732 A1 | 10/2005 | Rush |
| 2004/0171921 A1 | 9/2004 | Say et al. | | 2005/0238503 A1 | 10/2005 | Rush et al. |
| 2004/0176913 A1 | 9/2004 | Kawatahara et al. | | 2005/0238507 A1 | 10/2005 | DiIanni et al. |
| 2004/0186362 A1 | 9/2004 | Brauker et al. | | 2005/0239154 A1 | 10/2005 | Feldman et al. |
| 2004/0186365 A1 | 9/2004 | Jin et al. | | 2005/0239518 A1 | 10/2005 | D'Agostino et al. |
| 2004/0193025 A1 | 9/2004 | Steil et al. | | 2005/0245795 A1 | 11/2005 | Goode, Jr. et al. |
| 2004/0193090 A1 | 9/2004 | Lebel et al. | | 2005/0245799 A1 | 11/2005 | Brauker et al. |
| 2004/0199059 A1 | 10/2004 | Brauker et al. | | 2005/0249506 A1 | 11/2005 | Fuse |
| 2004/0202576 A1 | 10/2004 | Aceti et al. | | 2005/0249606 A1 | 11/2005 | Rush |

| | | |
|---|---|---|
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0094986 A1 | 5/2006 | Neel et al. |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0253085 A1 | 11/2006 | Geismar et al. |
| 2006/0273759 A1 | 12/2006 | Reggiardo |
| 2006/0282290 A1 | 12/2006 | Flaherty et al. |
| 2007/0016381 A1 | 1/2007 | Kamath et al. |
| 2007/0078323 A1 | 4/2007 | Reggiardo et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0103447 A1 | 5/2008 | Reggiardo et al. |
| 2008/0108942 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0257063 A1 | 10/2008 | Rush et al. |
| 2008/0262469 A1 | 10/2008 | Brister et al. |
| 2008/0267787 A1 | 10/2008 | Rush et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063402 A1 | 3/2009 | Hayter |
| 2009/0068954 A1 | 3/2009 | Reggiardo et al. |
| 2009/0076355 A1 | 3/2009 | Reggiardo |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105648 A1 | 4/2009 | Rush et al. |
| 2009/0105649 A1 | 4/2009 | Rush et al. |
| 2009/0112156 A1 | 4/2009 | Rush et al. |
| 2009/0112165 A1 | 4/2009 | Rush et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163869 A1 | 6/2009 | Rush et al. |
| 2009/0178459 A1 | 7/2009 | Li et al. |
| 2009/0182217 A1 | 7/2009 | Li et al. |

| | | |
|---|---|---|
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0008794 A1 | 1/2010 | Rush et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0019721 A1 | 1/2010 | Reggiardo |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0049130 A1 | 2/2010 | Rush et al. |
| 2010/0049131 A1 | 2/2010 | Rush et al. |
| 2010/0049132 A1 | 2/2010 | Rush et al. |
| 2010/0049133 A1 | 2/2010 | Rush et al. |
| 2010/0057007 A1 | 3/2010 | Rush et al. |
| 2010/0057038 A1 | 3/2010 | Rush et al. |
| 2010/0063373 A1 | 3/2010 | Kamath et al. |
| 2010/0063446 A1 | 3/2010 | Rush et al. |
| 2010/0063449 A1 | 3/2010 | Rush et al. |
| 2010/0068072 A1 | 3/2010 | Rush et al. |
| 2010/0076283 A1 | 3/2010 | Simpson et al. |
| 2010/0076371 A1 | 3/2010 | Rush et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100041 A1 | 4/2010 | Rush et al. |
| 2010/0100042 A1 | 4/2010 | Rush et al. |
| 2010/0114028 A1 | 5/2010 | Rush et al. |
| 2010/0114029 A1 | 5/2010 | Rush et al. |
| 2010/0114073 A1 | 5/2010 | Rush et al. |
| 2010/0119693 A1 | 5/2010 | Tapsak et al. |
| 2010/0121169 A1 | 5/2010 | Petisce et al. |
| 2010/0241076 A1 | 9/2010 | Rush et al. |
| 2010/0312177 A1 | 12/2010 | Rush et al. |

FOREIGN PATENT DOCUMENTS

| | | |
|---|---|---|
| EP | 0518524 | 12/1992 |
| EP | 0709573 | 5/1996 |
| EP | 0878707 | 11/1998 |
| EP | 0543916 | 7/2001 |
| EP | 1130638 | 9/2001 |
| EP | 1755443 | 11/2005 |
| EP | 1783536 | 5/2007 |
| FR | 2718492 | 10/1995 |
| JP | 1-080775 | 3/1989 |
| JP | 2001-177423 | 6/2001 |
| JP | 2001-056673 | 11/2001 |
| WO | WO-96/14026 | 5/1996 |
| WO | WO-96/34637 | 11/1996 |
| WO | WO-99/22236 | 5/1999 |
| WO | WO-01/41849 | 6/2001 |
| WO | WO-01/52727 | 7/2001 |
| WO | WO-01/71186 | 9/2001 |
| WO | WO 0171186 A2 * | 9/2001 |
| WO | WO-03/071930 | 2/2002 |
| WO | WO-02/39086 | 5/2002 |
| WO | WO-02/057627 | 7/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-03/090509 | 4/2003 |
| WO | WO-03/103763 | 12/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO-2008/055037 | 5/2008 |
| WO | WO-2008/110267 | 9/2008 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

Canadian Patent Application No. 2,604,358, Examiner's Report mailed Feb. 9, 2010.

Canadian Patent Application No. 2,604,358, Examiner's Report mailed Jun. 30, 2009.

Canadian Patent Application No. 2,604,498, Examiner's Report mailed Jul. 16, 2009.

Canadian Patent Application No. 2,604,695, Examiner's Report mailed Apr. 9, 2010.

Chinese Patent Application No. 200680018051.0, Original Language and English Translation of First Office Action mailed Apr. 20, 2009.

Chinese Patent Application No. 200680018073.7, Original Language and English Translation of First Office Action mailed Jan. 23, 2009.

European Patent Application No. 03770727.0, Supplementary European Search Report mailed Jun. 12, 2008.

European Patent Application No. 06750300.3, Extended European Search Report mailed Aug. 20, 2009.

PCT Application No. PCT/US2003/032191, International Preliminary Examination Report mailed Jan. 4, 2005.

PCT Application No. PCT/US2003/032191, International Search Report and Written Opinion of the International Searching Authority mailed Apr. 1, 2004.

PCT Application No. PCT/US2006/014022, International Preliminary Report on Patentability and Written Opinion of the International Searching Authority mailed Oct. 25, 2007.
PCT Application No. PCT/US2006/014022, International Search Report and Written Opinion of the International Searching Authority mailed May 23, 2007.
PCT Application No. PCT/US2006/014228, International Preliminary Report on Patentability and Written Opinion of the International Searching Authority mailed Oct. 25, 2007.
PCT Application No. PCT/US2006/014228, International Search Report and Written Opinion of the International Searching Authority mailed May 26, 2007.
PCT Application No. PCT/US2006/014281, International Preliminary Report on Patentability and Written Opinion of the International Searching Authority mailed Oct. 25, 2007.
PCT Application No. PCT/US2006/014281, International Search Report and Written Opinion of the International Searching Authority mailed Feb. 22, 2007.
U.S. Appl. No. 11/106,155, Office Action mailed Aug. 13, 2009.
U.S. Appl. No. 11/106,155, Office Action mailed Jan. 14, 2010.
U.S. Appl. No. 11/106,155, Office Action mailed May 19, 2010.
U.S. Appl. No. 11/106,155, Office Action mailed Oct. 29, 2008.
U.S. Appl. No. 11/106,256, Notice of Allowance mailed Apr. 18, 2008.
U.S. Appl. No. 12/345,554, Office Action mailed May 4, 2010.
U.S. Appl. No. 12/345,554, Office Action mailed Oct. 13, 2009.
U.S. Appl. No. 12/345,563, Office Action mailed Jun. 1, 2010.
U.S. Appl. No. 12/345,571, Office Action mailed Jun. 29, 2010.
U.S. Appl. No. 12/345,586, Office Action mailed Jul. 27, 2010.
U.S. Appl. No. 12/345,591, Office Action mailed Jul. 27, 2010.
U.S. Appl. No. 12/345,595, Notice of Allowance mailed May 6, 2010.
U.S. Appl. No. 12/345,595, Office Action mailed Jan. 12, 2010.
U.S. Appl. No. 12/345,597, Notice of Allowance mailed May 14, 2010.
U.S. Appl. No. 12/345,597, Office Action mailed Jan. 11, 2010.
U.S. Appl. No. 12/345,603, Notice of Allowance mailed May 13, 2010.
U.S. Appl. No. 12/345,603, Office Action mailed Dec. 31, 2009.
Canadian Patent Application No. 2,604,695, Notice of Allowance mailed Nov. 22, 2010.
European Patent Application No. 10013445.1 European Search Report mailed Apr. 14, 2011.
European Patent Application No. 10013449.3 European Search Report mailed Jan. 31, 2011.
PCT Application No. PCT/US2003/032191, International Search Report of the International Searching Authority mailed Apr. 1, 2004.
PCT Application No. PCT/US2006/014281, International Search Report and Written Opinion of the International Searching Authority mailed Feb. 22, 2007.
U.S. Appl. No. 11/105,711, Advisory Action mailed Apr. 2, 2009.
U.S. Appl. No. 11/105,711, Notice of Allowance mailed Apr. 12, 2010.
U.S. Appl. No. 11/105,711, Office Action mailed Jun. 2, 2009.
U.S. Appl. No. 11/105,711, Office Action mailed Mar. 21, 2008.
U.S. Appl. No. 11/105,711, Office Action mailed Oct. 17, 2008.
U.S. Appl. No. 11/105,711, Office Action mailed Oct. 30, 2009.
U.S. Appl. No. 11/106,256, Notice of Allowance mailed Apr. 18, 2008.
U.S. Appl. No. 11/106,256, Office Action mailed Jan. 24, 2008.
U.S. Appl. No. 11/106,256, Office Action mailed May 3, 2007.
U.S. Appl. No. 12/345,554, Advisory Action mailed Jul. 13, 2010.
U.S. Appl. No. 12/345,554, Notice of Allowance mailed Jun. 10, 2011.
U.S. Appl. No. 12/345,554, Office Action mailed May 4, 2010.
U.S. Appl. No. 12/345,554, Office Action mailed Nov. 22, 2010.
U.S. Appl. No. 12/345,554, Office Action mailed Oct. 13, 2009.
U.S. Appl. No. 12/345,563, Notice of Allowance mailed Jul. 25, 2011.
U.S. Appl. No. 12/345,563, Office Action mailed Apr. 8, 2011.
U.S. Appl. No. 12/345,563, Office Action mailed Jun. 1, 2010.
U.S. Appl. No. 12/345,563, Office Action mailed Sep. 28, 2010.
U.S. Appl. No. 12/345,571, Notice of Allowance Dec. 7, 2010.
U.S. Appl. No. 12/345,571, Office Action mailed Jun. 29, 2010.
U.S. Appl. No. 12/345,586, Office Action mailed Dec. 27, 2010.
U.S. Appl. No. 12/345,586, Office Action mailed Jul. 27, 2010.
U.S. Appl. No. 12/345,591, Office Action mailed Jan. 6, 2011.
U.S. Appl. No. 12/345,591, Office Action mailed Jul. 27, 2010
U.S. Appl. No. 12/345,595, Notice of Allowance mailed May 6, 2010.
U.S. Appl. No. 12/345,595, Office Action mailed Jan. 12, 2010.
U.S. Appl. No. 12/345,597, Notice of Allowance mailed May 14, 2010.
U.S. Appl. No. 12/345,597, Office Action mailed Jan. 11, 2010.
U.S. Appl. No. 12/345,603, Notice of Allowance mailed May 13, 2010.
U.S. Appl. No. 12/345,603, Office Action mailed Dec. 31, 2009.
U.S. Appl. No. 12/562,296, Office Action mailed Oct. 21, 2010.
U.S. Appl. No. 12/563,502, Notice of Allowance mailed Feb. 23, 2011.
U.S. Appl. No. 12/563,502, Office Action mailed Aug. 4, 2010.
U.S. Appl. No. 12/563,502, Office Action mailed Jan. 5, 2011.
U.S. Appl. No. 12/565,130, Notice of Allowance mailed Mar. 2, 2011.
U.S. Appl. No. 12/565,130, Office Action mailed Aug. 4, 2010.
U.S. Appl. No. 12/565,130, Office Action mailed Jan. 5, 2011.
U.S. Appl. No. 12/565,146, Office Action mailed Nov. 29, 2010.

* cited by examiner

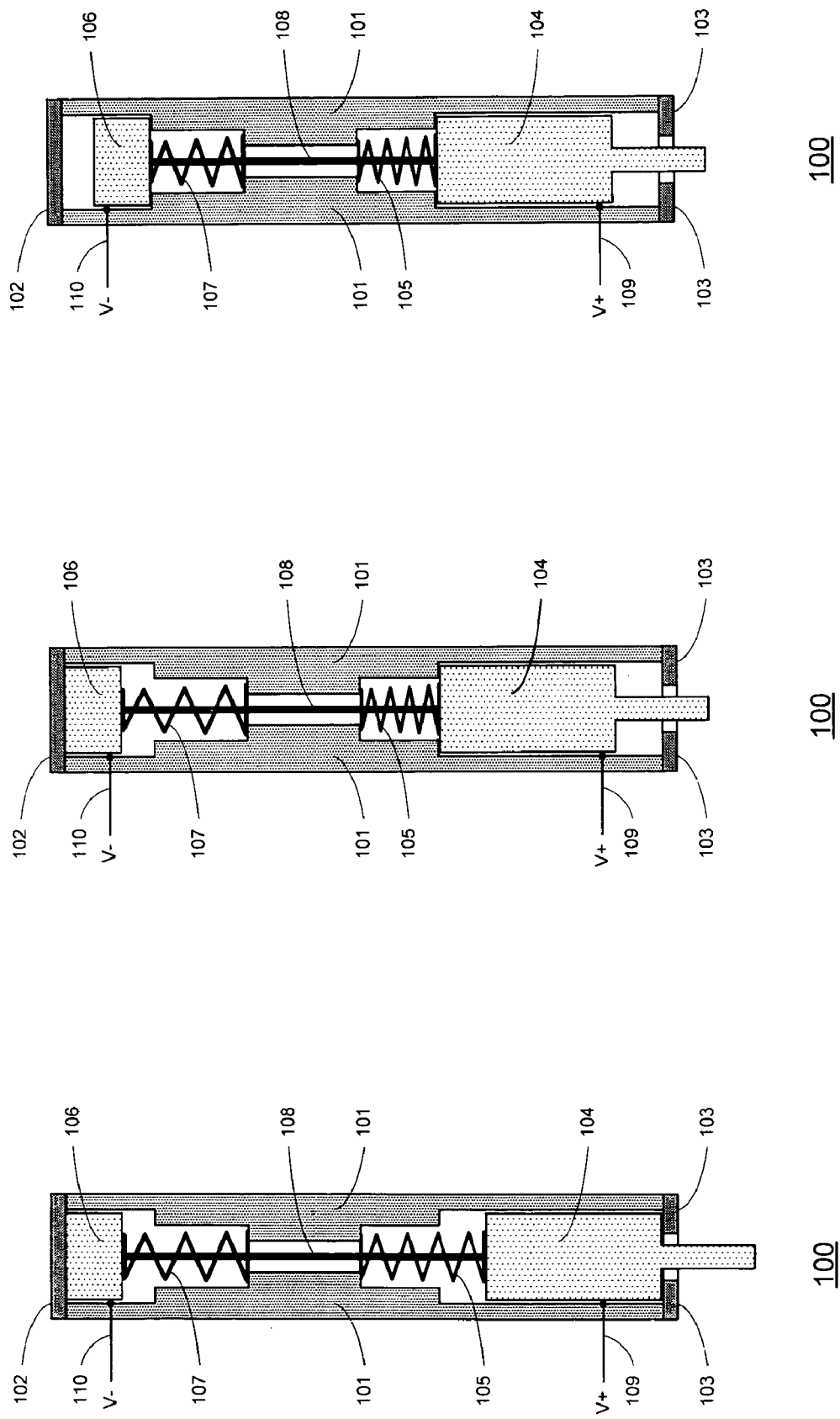

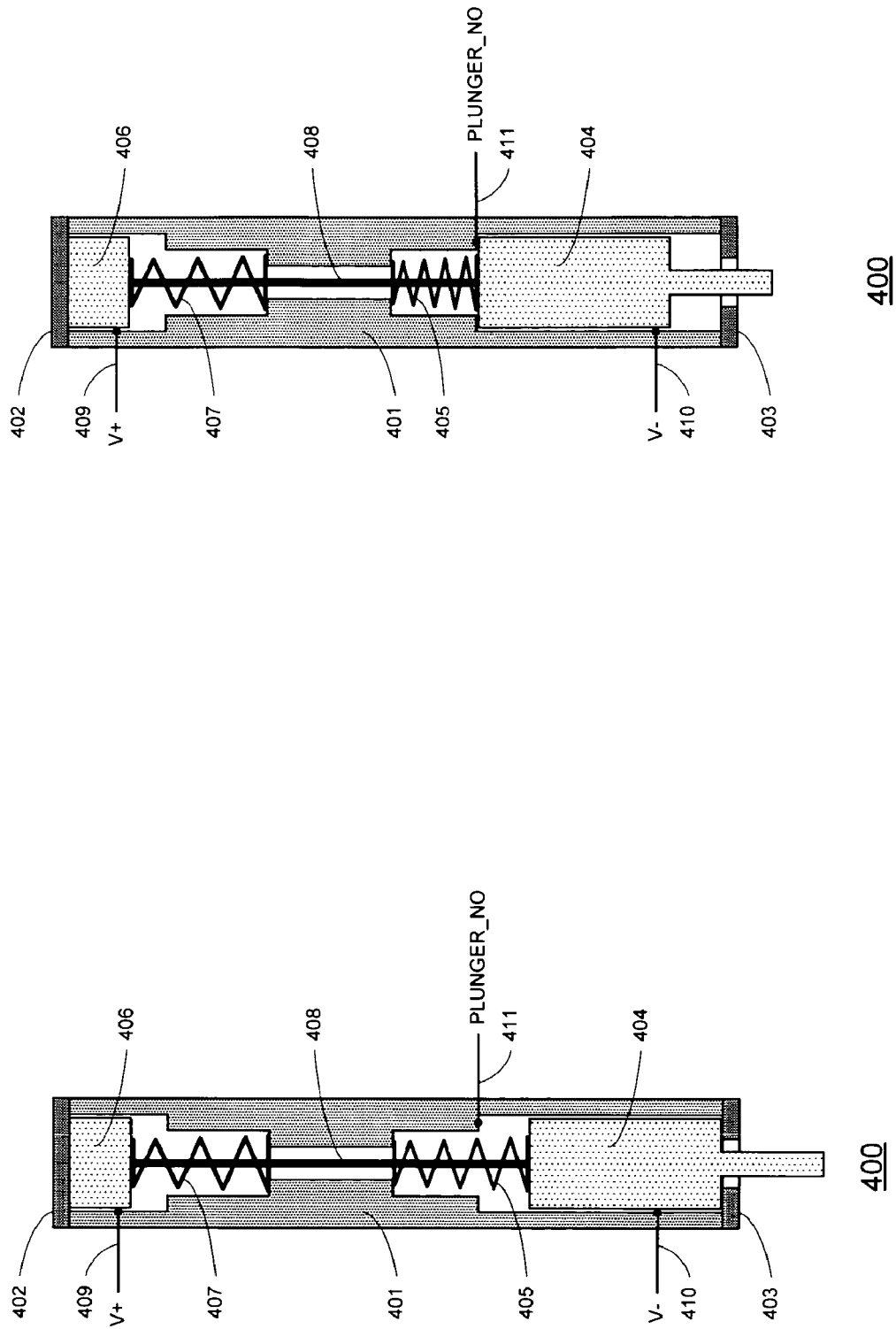

900

900

VARIABLE VOLUME, SHAPE MEMORY ACTUATED INSULIN DISPENSING PUMP

CROSS REFERENCE TO RELATED APPLICATIONS

The present application is a divisional application of pending U.S. application Ser. No. 11/106,155 filed Apr. 13, 2005 which is a continuation-in-part of U.S. application Ser. No. 10/683,659 of Benjamin M. Rush et al., filed on Oct. 9, 2003, and issued as U.S. Pat. No. 6,916,159 on Jul. 12, 2005, which is related to and claims priority based on U.S. Provisional Application No. 60/417,464, entitled "Disposable Pump for Drug Delivery System," filed on Oct. 9, 2002, and U.S. Provisional Application No. 60/424,613, entitled "Disposable Pump and Actuation Circuit for Drug Delivery System," filed on Nov. 6, 2002, each of which is hereby incorporated by this reference in its entirety. The present application is related to U.S. application Ser. No. 11/105,711 of Benjamin M. Rush, entitled "Fluid Delivery Device with Auto Calibration," and U.S. application Ser. No. 11/106,256 of Benjamin M. Rush, entitled "Devices and Methods For Use in Assessing a Flow Condition of a Fluid," each of which was filed Apr. 13, 2005 and are hereby incorporated herein, in their entirety, by this reference.

FIELD OF THE INVENTION

The present invention is generally related to portable insulin or other liquid delivery systems and more specifically related to a pump for use in such systems.

BACKGROUND OF THE INVENTION

Insulin pumps are widely available and are used by diabetic people to automatically deliver insulin over extended periods of time. Many currently available insulin pumps employ a common pumping technology, the syringe pump. In a syringe pump, the plunger of the syringe is advanced by a lead screw that is turned by a precision stepper motor. As the plunger advances, fluid is forced out of the syringe, through a catheter to the patient. The choice of the syringe pump as a pumping technology for insulin pumps is motivated by its ability to precisely deliver the relatively small volume of insulin required by a typical diabetic (about 0.1 to about 1.0 $cm^3$ per day) in a nearly continuous manner. The delivery rate of a syringe pump can also be readily adjusted through a large range to accommodate changing insulin requirements of an individual (e.g., basal rates and bolus doses) by adjusting the stepping rate of the motor. While the syringe pump is unparalleled in its ability to precisely deliver a liquid over a wide range of flow rates and in a nearly continuous manner, such performance comes at a cost. Currently available insulin pumps are complicated and expensive pieces of equipment costing thousands of dollars. This high cost is due primarily to the complexity of the stepper motor and lead screw mechanism. These components also contribute significantly to the overall size and weight of the insulin pump. Additionally, because of their cost, currently available insulin pumps have an intended period of use of up to two years, which necessitates routine maintenance of the device such as recharging the power supply and refilling with insulin. These syringe type pumps, even if described as disposable, are simply too expensive to be truly disposable, or are alternatively disposed at a very high cost to patients and insurance companies alike.

Shape memory alloys are a part of a class of materials that change shape when power is applied to them but that return to their natural state when the power is removed. The materials can be used to form an actuator by harnessing this unique attribute of the materials. A pump can be made with a shape memory alloy actuator. However, a shape memory alloy does not have the inherent accuracy and repeatability of the precision stepper motor used in a syringe pump. Although price is always important, precision is also essential in a pump used to deliver insulin or other drugs. It is therefore necessary to provide a system to precisely control and actuate a pump utilizing a shape memory material as an actuator.

SUMMARY OF INVENTION

The present invention employs a cost effective yet precise pumping system and method to deliver insulin or other liquid to a user. Unique physical design aspects and an intelligent control system employed in the present invention allow for a shape memory alloy to actuate a pumping mechanism with excellent reliability and repeatability.

The present invention allows for not only a cost effective pumping system, but also for a robust, precise, light weight, and fault tolerant system. Although the pumping system is precise, light weight, and fault tolerant, in the medical applications where the pump will be most advantageous, numerous reasons may make it desirable to dispose of and replace portions of the pumping system relatively frequently. The low cost of the pumping mechanism of the present invention allows for such disposable usage, while at the same time the pump is able to provide precision doses throughout the life of the pump. Stresses in the pump are minimized with the control system, and warnings can be generated if the pump is not primed properly or if an occlusion is detected within the pumping system. The reduction of stresses within the pump provides for a smaller and lighter weight pump with a longer lifetime, which is of obvious benefit to a user of the pump. Furthermore, the intelligent control system allows the pump to operate even if a fault is detected. For example, if the full stroke of the pump is unavailable for some reason, a lesser stroke can be utilized (at a higher frequency) and the pump can continue to provide the necessary dosage to the user.

Additional aspects, advantages and features of the present invention are included in the following description of exemplary examples thereof, which description should be taken in conjunction with the accompanying figures, and wherein like (and similar) numerals are used to describe the same feature throughout the figures. While the prefix of a numbering element may change based upon the figure number, if the remainder of the numbering element is the same in the various embodiments, the component is the same or similar to that described regarding an earlier described embodiment. For example, capacitor 304 of FIG. 3 is the same or similar to capacitor 504 of FIG. 5. When this is the case, the element will not be described again, and reference should be made to the description of the earlier figure (FIG. 3 in this example). All patents, patent applications, articles and other publications referenced herein are hereby incorporated herein by this reference in their entirety for all purposes.

BRIEF DESCRIPTION OF THE DRAWINGS

FIGS. 1A, 1B, and 1C illustrate pump 100 at various stages of operation.

FIGS. 4A and 4B illustrate pump 400 at various stages of operation.

DETAILED DESCRIPTION OF THE PREFERRED EMBODIMENTS

Figure 1D:
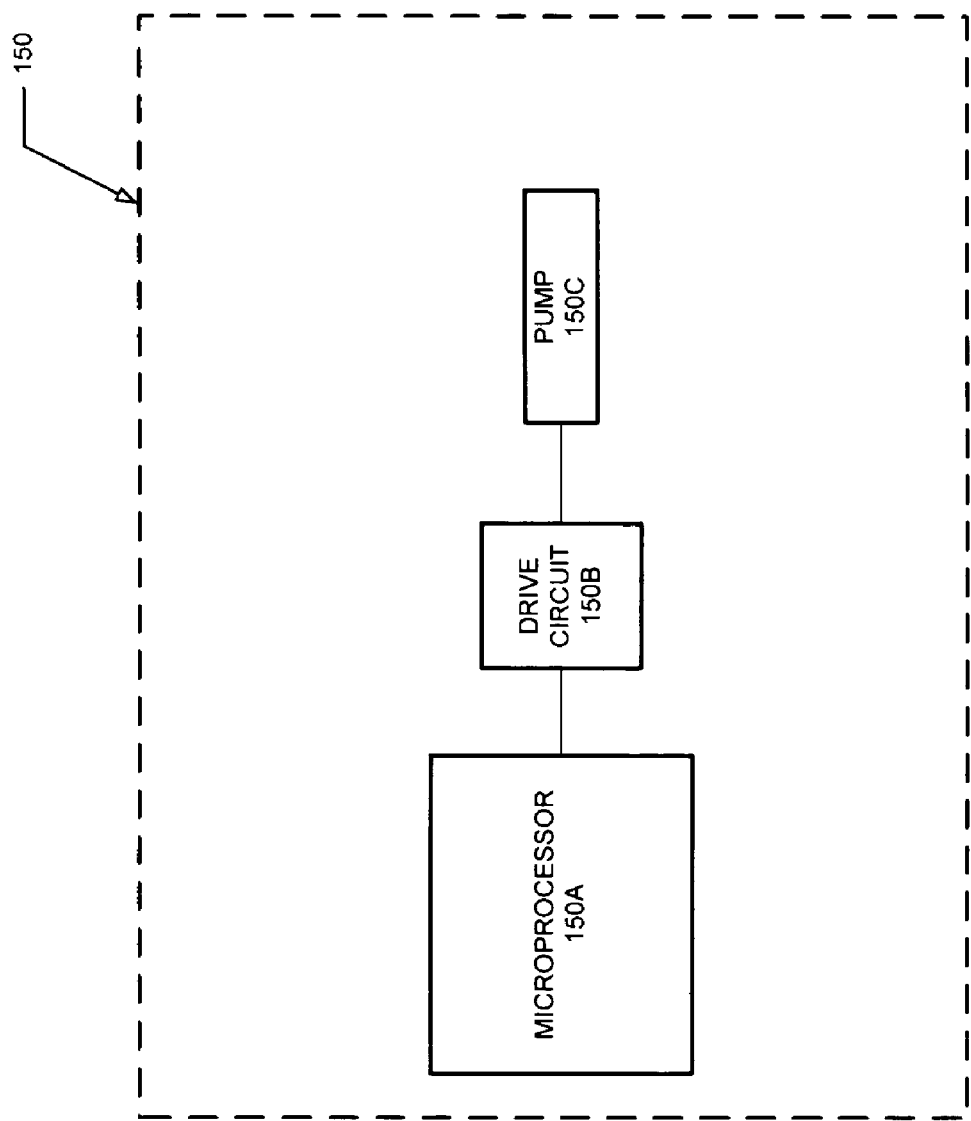
FIG. 1D is a block diagram of pumping system or "pump" 150.

The present invention employs a cost effective yet precise pumping system and method to deliver insulin or other liquid to a user. Unique physical design aspects and an intelligent control system employed in the present invention allow for a shape memory alloy to actuate a pumping mechanism with excellent reliability and repeatability.

The present invention allows for not only a cost effective pumping system, but also for a robust, precise, light weight, and fault tolerant system. Although the pumping system is precise, light weight, and fault tolerant, in the medical applications where the pump will be most advantageous, numerous reasons may make it desirable to dispose of and replace portions of the pumping system relatively frequently. The low cost of the pumping mechanism of the present invention allows for such disposable usage, while at the same time the pump is able to provide precision doses throughout the life of the pump. Stresses in the pump are minimized with the control system, and warnings can be generated if the pump is not primed properly or if an occlusion is detected within the pumping system. The reduction of stresses within the pump provides for a smaller and lighter weight pump with a longer lifetime, which is of obvious benefit to a user of the pump. Furthermore, the intelligent control system allows the pump to operate even if a fault is detected. For example, if the full stroke of the pump is unavailable for some reason, a lesser stroke can be utilized (at a higher frequency) and the pump can continue to provide the necessary dosage to the user.

As mentioned briefly above, a shape memory alloy is used to actuate a pump made in accordance with the present invention. In the process of undergoing a dimensional change, the shape memory material goes through a reversible phase transition or transformation, or a reversible structural phase transition, upon a change in temperature. Generally, such a transition represents a change in the material from one solid phase of the material to another, for example, by virtue of a change in the crystal structure of the material or by virtue of a reordering of the material at a molecular level. In the case of nitinol, for example, the superelastic alloy has a low temperature phase, or martensitic phase, and a high temperature phase, or austenitic phase. These phases can also be referred to in terms of a stiff phase and a soft and malleable phase, or responsive phase. The particular phase transition associated with a particular alloy material may vary. Shape memory materials are well understood by those of ordinary skill in the art.

Pump 100, an embodiment of a pump (or a portion thereof) of the present invention, is shown in the inactive state in FIG. 1A, the fully activated state in FIG. 1B, and the stress-loaded state in FIG. 1C. The pump body comprises a case 101, a top cap 102, and a plunger cap 103. Within the pump is a plunger 104 that is normally (in the inactive state) held against the plunger cap 103 by a plunger bias spring 105. Similarly, an overload piston 106 is normally (in inactive state) held against the top cap 102 by an overload piston spring 107 which is stronger (has a higher spring constant k) than the plunger bias spring 105. The plunger 104 is connected to the overload piston 106 by a shape memory alloy wire 108 which contracts when heated by a pulse or pulses of current flowing from the V+ 109 contact to the V− 110 contact through the shape memory alloy wire 108 where the V− 110 contact may be the system ground (GND) reference. The power in each pulse is determined by the voltage applied to the shape memory alloy wire 108 through the V+ 109 and V− 110 contacts. It is worth noting that the case is made of an insulating material while the plunger 104 and overload piston 106 are either made of a conductive material (e.g. metal) or are coated with an appropriately conductive material. The top cap 102 and plunger cap 103 may be made of insulating or conductive material as is best suited to a given design.

FIG. 1A shows the pump in the inactive state where the shape memory alloy wire 108 is not contracted, the plunger 104 is held against the plunger cap 103 by the plunger bias spring 105 and the overload piston 106 is held against the top cap 102 by the overload piston spring 107. This is the state to which the pump 100 returns after each activation or pumping cycle.

FIG. 1B shows the pump in the fully activated state where the shape memory alloy wire 108 has contracted enough to pull the plunger 104 up against a stop built into the case 101 without moving, while overload piston 106 which is held against the top cap 102 by the overload piston spring 107. This state realizes a full stroke of the plunger 104.

FIG. 1C shows the pump in the stress-loaded state where the shape memory alloy wire 108 has contracted sufficiently to pull the overload piston 106 up against a second stop built into the case 101. In this state the case 101, plunger 104, overload piston 106, and shape memory alloy wire 108 are under maximum stress.

The design of the basic pump 100 is such that there is no feedback to the circuit driving the pump (open loop) and the action of the pump after the fully activated state shown in FIG. 1B is accommodated by the design margin to ensure that the pump reaches a fully activated state. If the pulse or pulses of current applied to the shape memory alloy wire 108 are reduced to the minimum value required to achieve the fully activated state under worst case conditions, such as a cold wire, then the action of the basic pump 100 under best case conditions, such as a warm wire, will drive the pump toward the stress-loaded state shown in FIG. 1C. The design of the pump 100, and the selection of the overload piston spring 107 is driven by the differences between the worst-case and best-case conditions. Under normal operating (non-fault) conditions the pump always completes the full stroke (the fully activated state) as shown in FIG. 1B and operates reliably over the expected life of the pump because excess contraction and the resultant stress are minimized (as seen in the stress-loaded state shown in FIG. 1C). Considerations for the worst-case and best-case conditions include operating temperature range, the minimum pumping rate (e.g. the minimum basal delivery rate), and the maximum pumping rate (e.g. the maximum bolus rate).

It is important to note that the open-loop design of pump 100 lacks feedback and thus cannot adaptively accommodate faults as they are not sensed. For example, a pump failure such as a jammed plunger 104 could cause a reduced or zero insulin delivery output and the pump would be assumed by the user (patient) to be operating correctly when an improper dose was delivered.

FIG. 1D is a block diagram that shows the overall system of which the various pump embodiments are a part. The overall system 150 comprises a microprocessor 150A, drive circuitry 150B, and pump element 150C. All of these components can be considered to form the pump, even though pump element 150C alone is also sometimes referred to as the pump among those skilled in the art. Many different embodiments of the pump 150C and of a portion of the drive circuitry 150B are described in detail below, and throughout the application. In an insulin delivery system 150, all of the components (that are shown) may be packaged together or alternatively they may be grouped separately. For example, it may be desirable to group the pump and drive circuitry together while remotely locating the pump element. Other components such as user input devices and a display are not shown, but are all controlled by the processor in conjunction with the pump and drive circuitry.

Figure 2A:
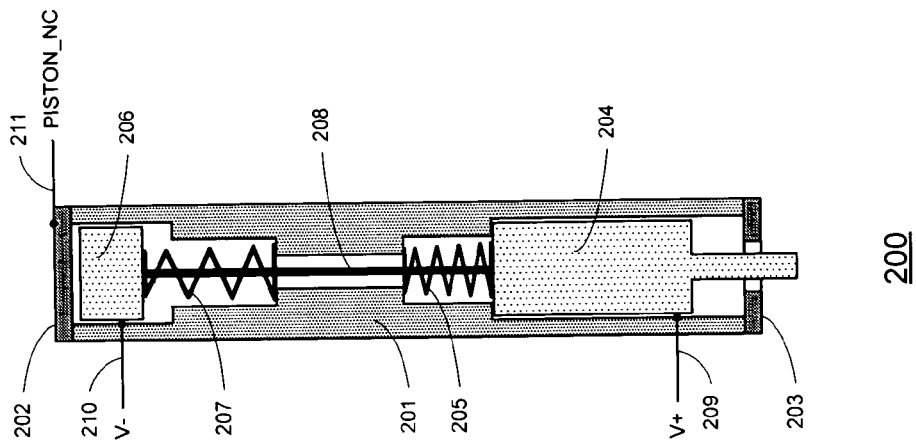
FIGS. 2A, 2B, and 2C illustrate pump 200 at various stages of operation.
Figure 2B:
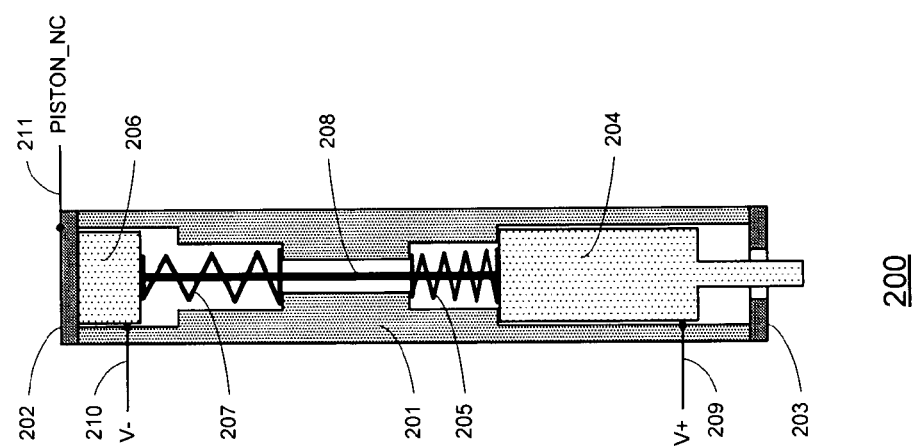
Figure 2C:
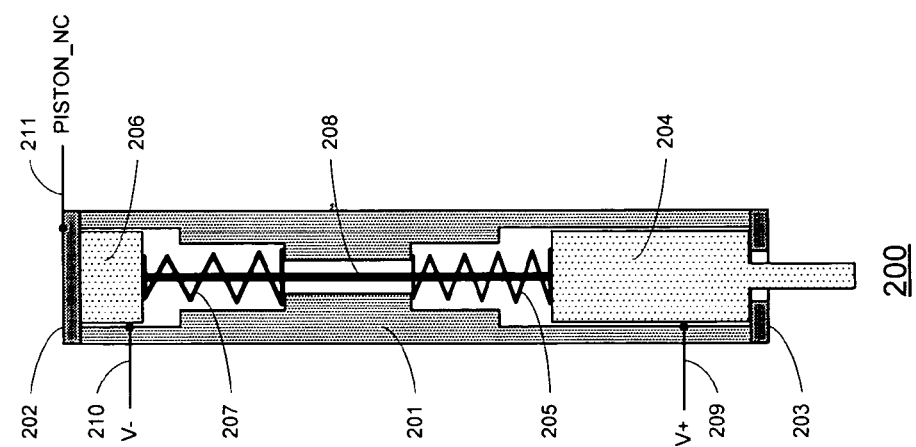

Another embodiment is illustrated in FIG. 2. The design shown in FIG. 2 comprises feedback that indicates the completion of the fully activated state but is otherwise similar to the pump shown in FIG. 1. The pump 200 incorporates feedback from a switch ("PISTON_NC 211") that indicates that the overload piston 206 is at the top of the pump or in contact with top cap 202. A switch, such as switch 211 (that provides feedback) may alternatively be referenced for the feedback it provides in the following description. The pump with PISTON_NC 211 feedback shown in FIG. 2 is constructed and operates in a similar fashion to the basic pump 100 shown in FIG. 1. The feedback comes from a normally-closed (NC) switch that indicates the overload piston 206 is in contact with the top cap 202 as in FIG. 2A and FIG. 2B. When the pump 200 enters the overload state as shown in FIG. 2C then the switch opens and feedback is fed to the drive circuit. If the feedback is not received during the maximum pulse period used for pump 100 then an error has occurred and pump 200 operation can be discontinued. The PISTON_NC 211 feedback is shown as connected directly to the top cap 202 which indicates that the top cap 202 is either made of a conductive material (e.g. metal) or is coated with an appropriately conductive material. If the design of a given pump requires the top cap 202 to be made of an insulating material then the PISTON_NC 211 feedback can be moved to the inner surface of the top cap 202 so that the PISTON_NC 211 feedback is in direct contact with the overload piston 206 in the inactive state as shown in FIG. 2A.

An advantage of pump 200 is fault detection based on the feedback from (normally closed) switch 211 (if the switch is not activated in the maximum pulse duration). The pump also saves energy because it terminates the activation pulse when full pump action is achieved. Minimizing energy consumption is extremely important for a portable insulin pump, as it maximizes the time the pump can be used without inconveniencing the user.

FIG. 2C shows the pump in the stress-loaded state where the shape memory alloy wire 108 has contracted sufficiently to pull the overload piston 206 down, but not up against a stop built into the case 201. In this state, the case 201, plunger 204, overload piston 206 and shape memory alloy wire 208, are under stress. However, that stress is limited to the spring constant (k) of the overload piston spring 207 and is thus reduced as compared to the stress-loaded state shown in FIG. 1C where the overload piston 106 is against a hard stop of the case 101. The method used to further reduce the already minimized stress is the termination of the pulse or pulses of current that are flowing from the V+ 209 contact to the V− 210 contact through the shape memory alloy wire 208. This causes the shape memory alloy wire 208 to stop contracting and thus reduces the stress on the pump 200.

Figure 3A:
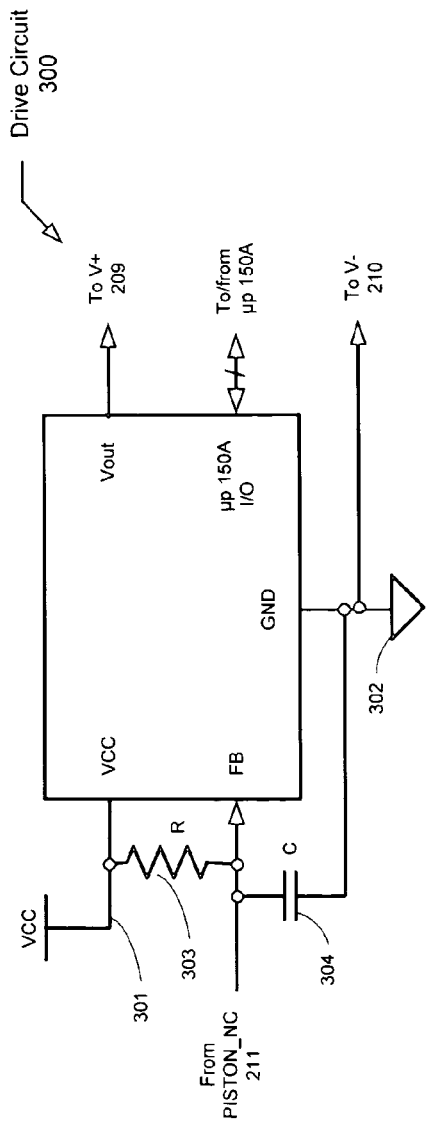
FIGS. 3A and 3B illustrate different embodiments of pump drive circuits for use with pump 200 or other pump embodiments.
Figure 3B:
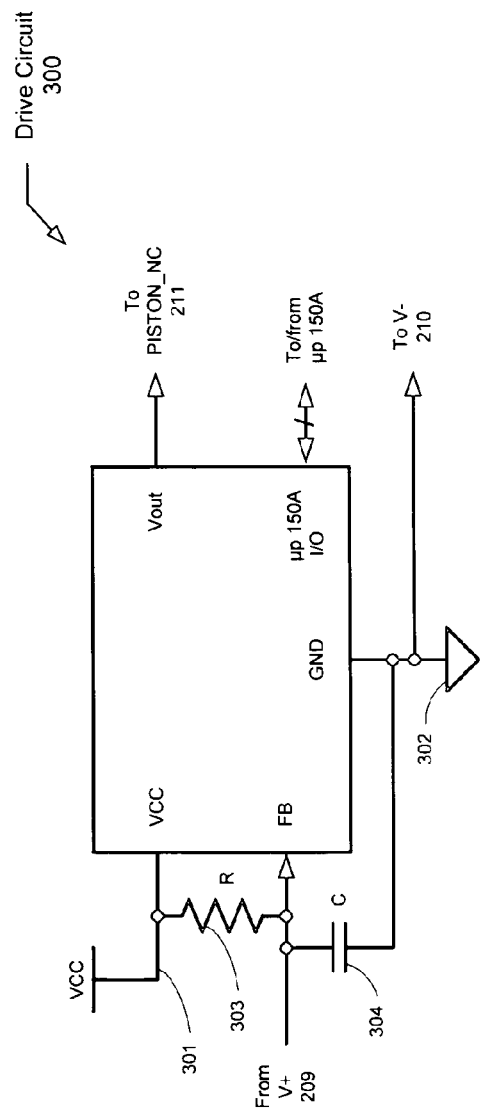

There are two primary methods to terminate the pulse or pulses to the shape memory alloy wire 208 as shown in FIG. 3A and FIG. 3B. The actual drive circuits are identical and the only difference between FIG. 3A and FIG. 3B is in the Voltage Output (Vout) and feedback connections as discussed below. Each drive circuit is connected to a power source VCC 301 and to the system ground GND 302. Each has a pull-up resistor R 303 from the feedback to VCC 301 and an optional filtering or "debounce" capacitor C 304 from the feedback to GND 302. The feedback is digital and detects a logic '0' when approximately 0V or GND 302 is present (i.e. the switch is closed) and a logic '1' when a voltage approximately equal to the supply voltage or VCC 301 is present (i.e. through the function of the pull-up resistor R 303 when the switch is opened). If the optional filtering or "debounce" capacitor C 304 is not present then the feedback may oscillate briefly when the switch opens or closes due to mechanical vibration related to the switch contact. If the optional filtering or "debounce" capacitor C 304 is present then the feedback actually detects the voltage on the capacitor C 304 which can not change instantaneously. When the switch closes the capacitor C 304 will be discharged quickly to approximately 0V or GND 302; when the switch opens the capacitor will be charged at a rate proportional to the values of the resistor R 303 and the capacitor C 304 to approximately the supply voltage or VCC 301. For example, a resistor R 303 value of 10,000 Ohms (10 kΩ) and a capacitor C 304 value of 100 pF would have a time-constant of one microsecond (1 µsec) and the state of the feedback would change from a logic '0' to a logic '1' in about two microseconds (2 µsec) without any oscillations (noise) on the feedback that could be acted upon by the drive circuit inappropriately.

The first method as shown in FIG. 3A is to connect the PISTON_NC 211 to the feedback to gate the drive signal Vout that is created by the drive circuit and which is connected to the pump V+ 209 contact. When the drive circuit receives feedback that the overload state is entered as shown in FIG. 2C then the pulse or pulses can be terminated and both the stress is reduced and power is saved. The second method as shown in FIG. 3B is to provide power to the pump 200 through the PISTON_NC 211 contact rather than the V+ 209 contact. This method automatically removes power from the shape memory alloy wire 208 whenever the PISTON_NC 211 switch opens as shown in FIG. 2C. If the feedback is ignored (i.e. the drive circuit is simplified to remove the feedback), then the overload piston 209 may oscillate between the states shown in FIG. 2B and FIG. 2C until the pulse or pulses from the drive circuit are terminated and only a partial power saving is realized. If the feedback is utilized as in FIG. 3A then when the drive circuit receives feedback that the overload state is entered as shown in FIG. 2C, the pulse or pulses can be terminated to prevent oscillations, and maximum power saving is realized as in the first method.

Addition of the PISTON_NC 211 feedback reduces the overall forces generated within the pump and allows the pump to be made smaller and lighter with improved reliability. Unfortunately, if the plunger 204 jams then the overload piston will begin moving and provide feedback that indicates the pump is operating properly. Again, a jammed plunger 204 could cause a reduced or zero insulin delivery output, but in this situation the pump would be assumed by the user (patient) to be operating correctly when in fact an improper dose may have been delivered.

Figure 5:
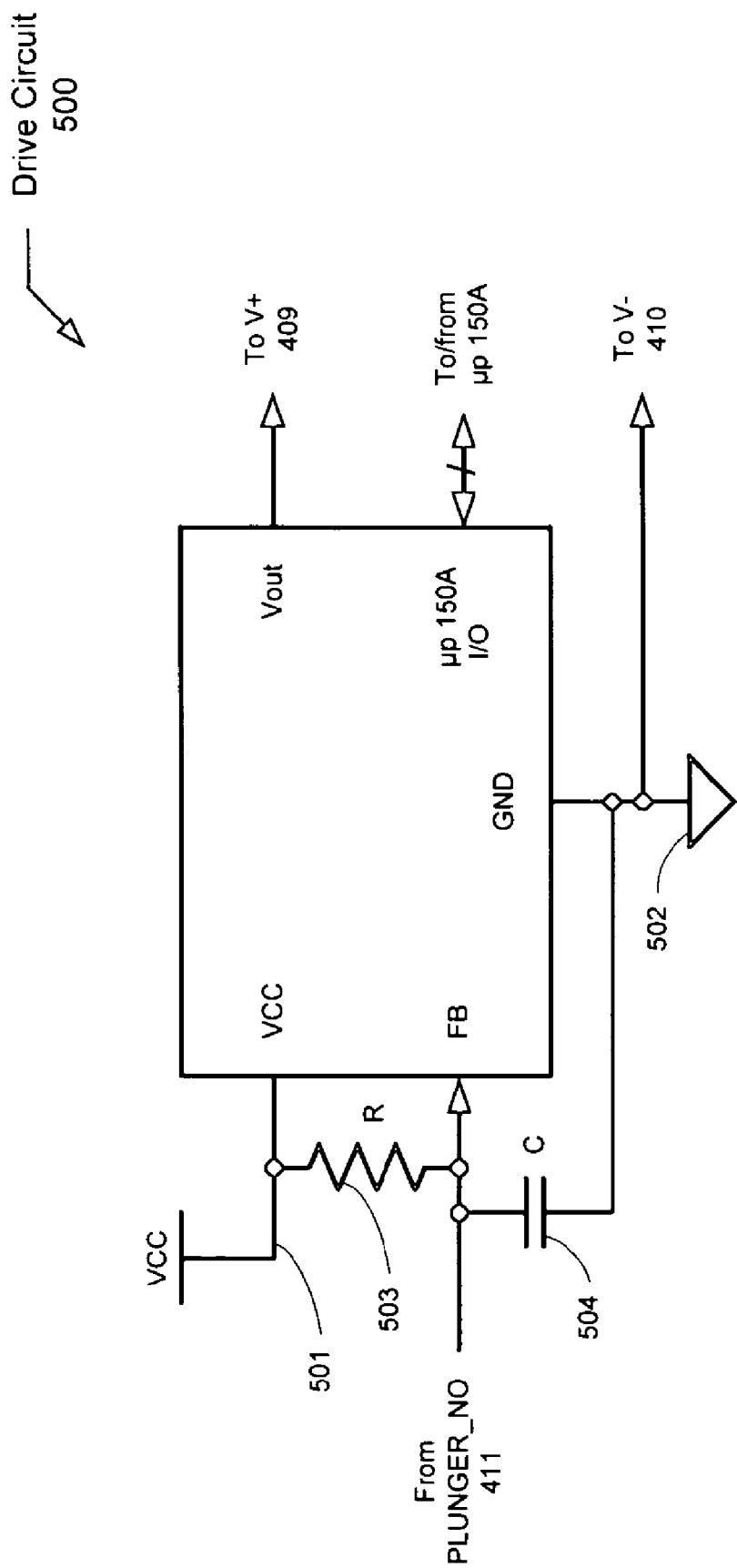
FIG. 5 illustrates an embodiment of a pump drive circuit for use with pump 400 or other pump embodiments.

Another embodiment of the invention is seen in pump 400 of FIGS. 4A and 4B. Pump 400 incorporates feedback that (more directly) indicates the completion of the fully activated state. Pump 400 uses (PLUNGER_NO) switch 411 to indicate that the plunger 404 is against the upper stop. This switch is used in place of (or in conjunction with) switch 211, and all of the feedback control and stress limitation features described with respect to pump 200 are present in pump 400. Drive circuit 500 seen in FIG. 5 is similar to drive circuit 300, as previously described. Pump 400 can also detect a fault with the pump if the plunger is not where it is expected to be based upon the potential applied to the actuator, as was also described previously. Similarly, the pump can detect a jam if the plunger is not where it is expected to be based upon the potential applied to the actuator.

Figure 6B:
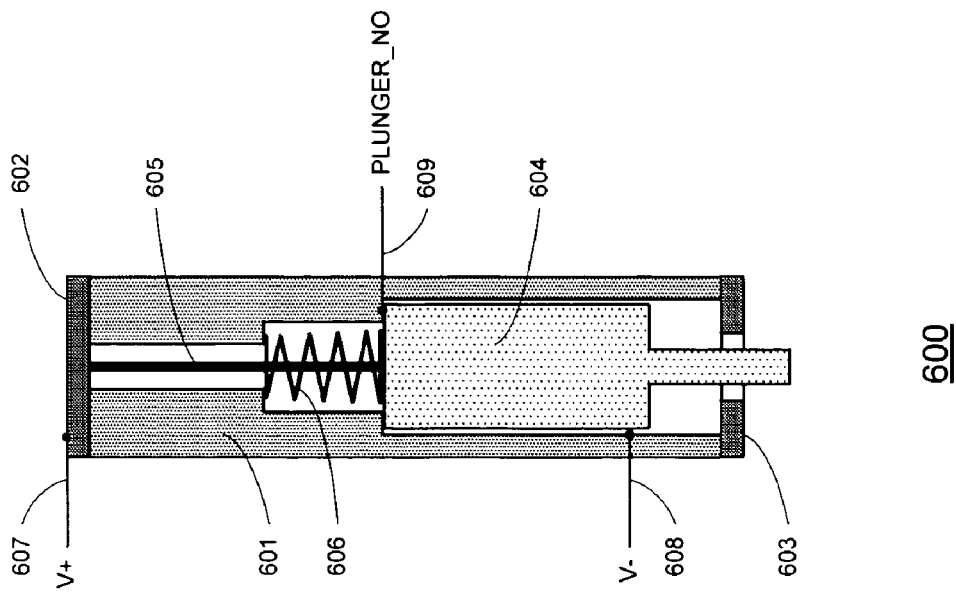
FIGS. 6A and 6B illustrate pump 600 at various stages of operation.
Figure 6A:
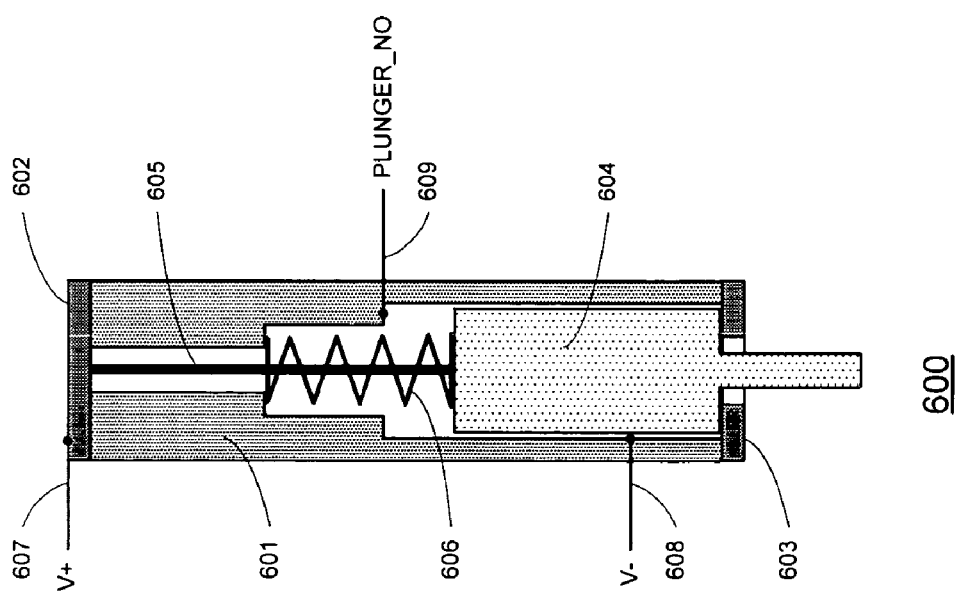

Another embodiment of the invention is seen in pump 600 of FIGS. 6A and 6B. Pump 600 is functionally the same as pump 400 but lacks overload piston 406 and overload spring 407. Because of the lack of these items, the top cap 607 preferably has some amount of compliance and acts as a simplified spring. Pump 600 has fewer parts and is thus lighter and smaller than pump 600. Fewer parts also generally result in improved reliability over the life of the pump.

Figure 7B:
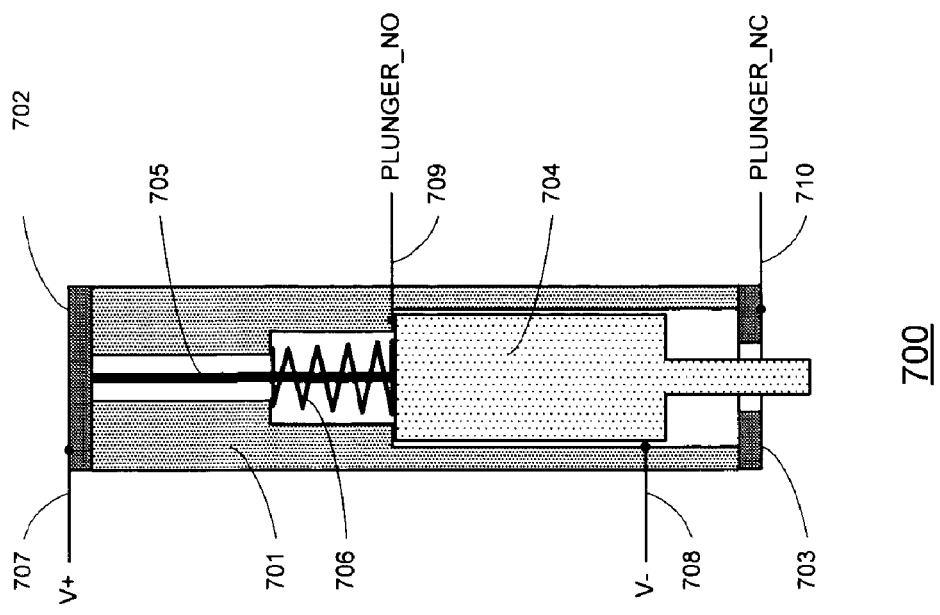
FIGS. 7A and 7B illustrate pump 700 at various stages of operation.
Figure 7A:
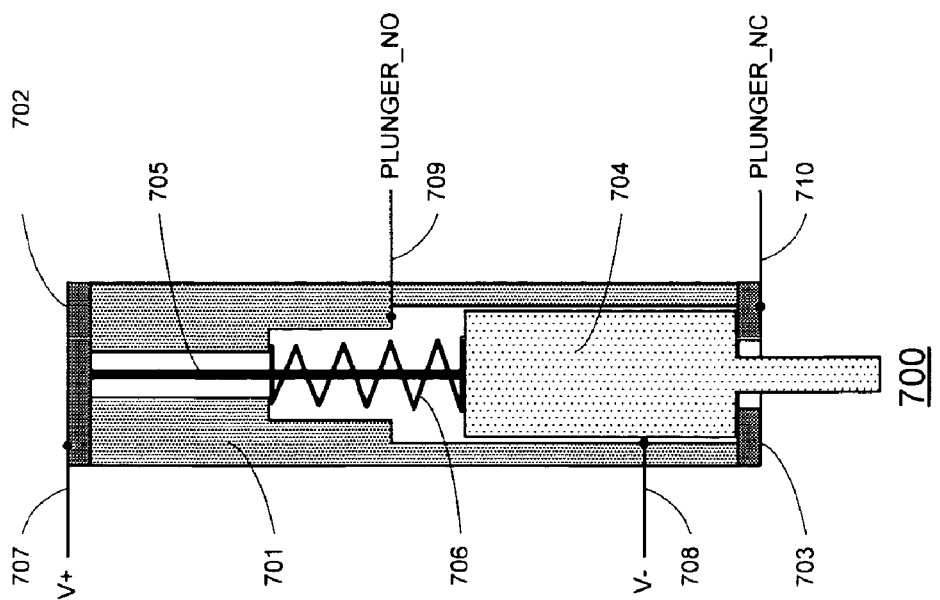

Yet another embodiment of the invention is seen in pump 700 of FIGS. 7A and 7B. Pump 700 is similar to pump 600 with the added advantage of feedback switch 710 (PLUNGER_NC) that directly indicates the completion of the fully activated state and return to the inactive state (at the completion of a pump cycle). Because pump 700 "knows" when a pump cycle is completed (and when it should be completed) it therefore "knows" when there is a fault, and can accommodate for the fault in what is known as a fault tolerant design. The fault tolerance is in both the direct measurement of the plunger 704 action and in ensuring that the plunger is resting in the fail safe state after the maximum permissible pump cycle time (this may also indicate a major occlusion in the pump system). If the power (GND) to the V− 708 contact is switched (via a series switch) to provide additional fault tolerance as is done in some pump systems, then the added feedback will also indicate the state of the V− 708 switch (not shown for clarity sake) as the value of switch 710 (PLUNGER_NC) will be 0V (GND) when the series power switch is closed and VCC when the series power switch is open. The pump can also detect an occlusion if the plunger does not return to the fully down state in the maximum pump cycle time.

Figure 8:
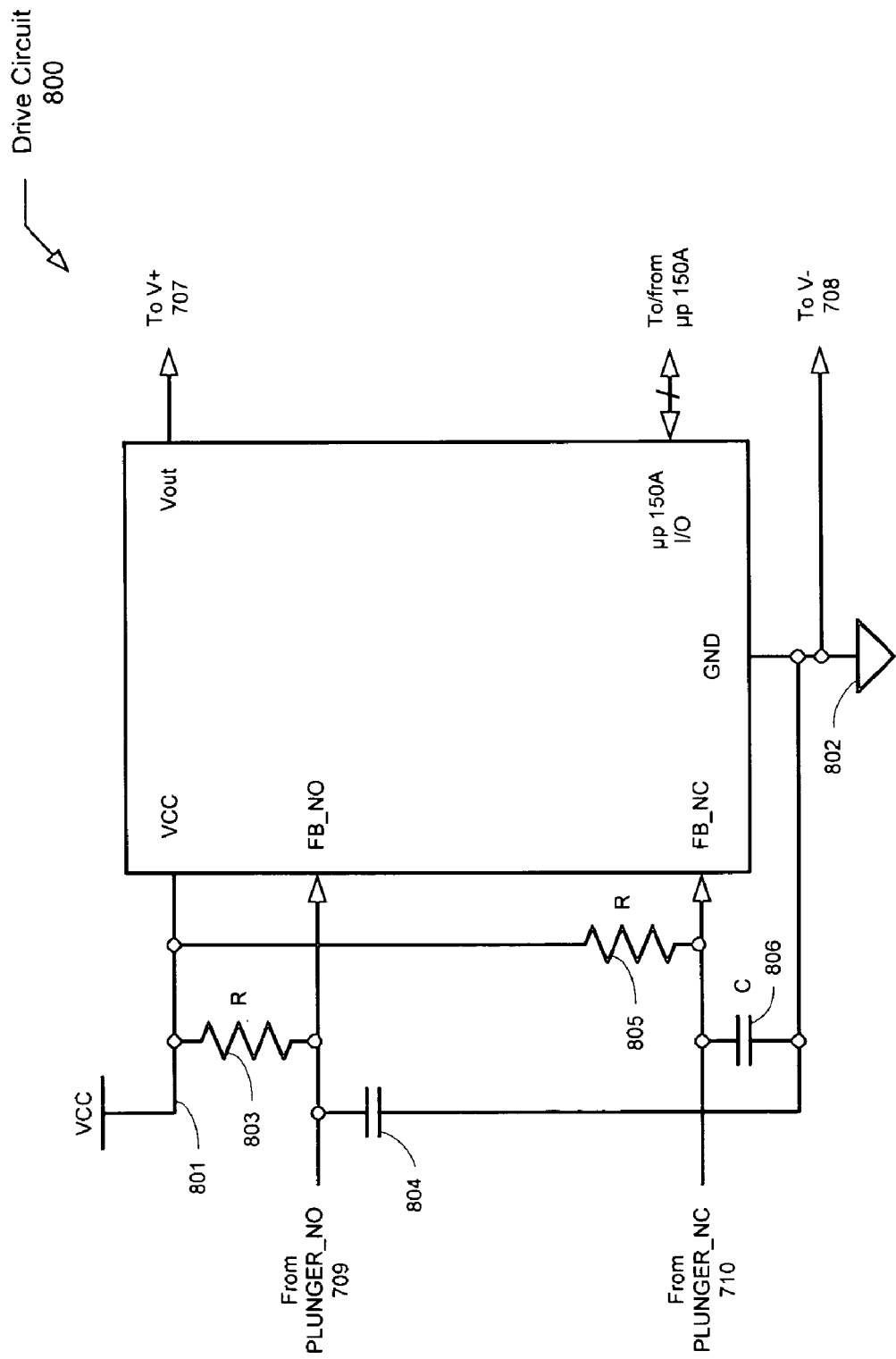
FIG. 8 illustrates an embodiment of a pump drive circuit for use with pump 700 or other pump embodiments.

The PLUNGER_NC 710 feedback is shown as connected directly to the plunger cap 703 which indicates that the plunger cap 703 is either made of a conductive material (e.g. metal) or is coated with an appropriately conductive material similar to the top cap 202 of FIG. 2. If the design of a given pump requires the plunger cap 703 to be made of an insulating material then the PLUNGER_NC 710 feedback can be moved to the inner surface of the plunger cap 703 so that the PLUNGER_NC 710 feedback is in direct contact with the plunger 704 in the inactive state as shown in FIG. 7A. Drive circuit 800 illustrated in FIG. 8 is similar to the drive circuits previously described. The pump 700 and drive circuit 800 comprise the minimum configuration for a fault tolerant system. All of the linear feedback techniques described below add fault resolution and improve fault tolerance at the expense of added cost and complexity.

Linear Feedback

Embodiments of a pump as previously described may also comprise linear feedback that directly indicates the position of the plunger. The linear feedback may be analog or digital and is used to detect the position of the plunger. The linear feedback may also indicate if there is a fault based upon the position of the plunger during various phases of operation of the pump. The linear feedback system can employ conductive encoding marks. This is a simple and economical way to detect the position of the plunger. Alternatively, optical position sensing utilizing optical encoding marks may be employed. This is more precise but is also more complex and expensive.

Figure 9B:
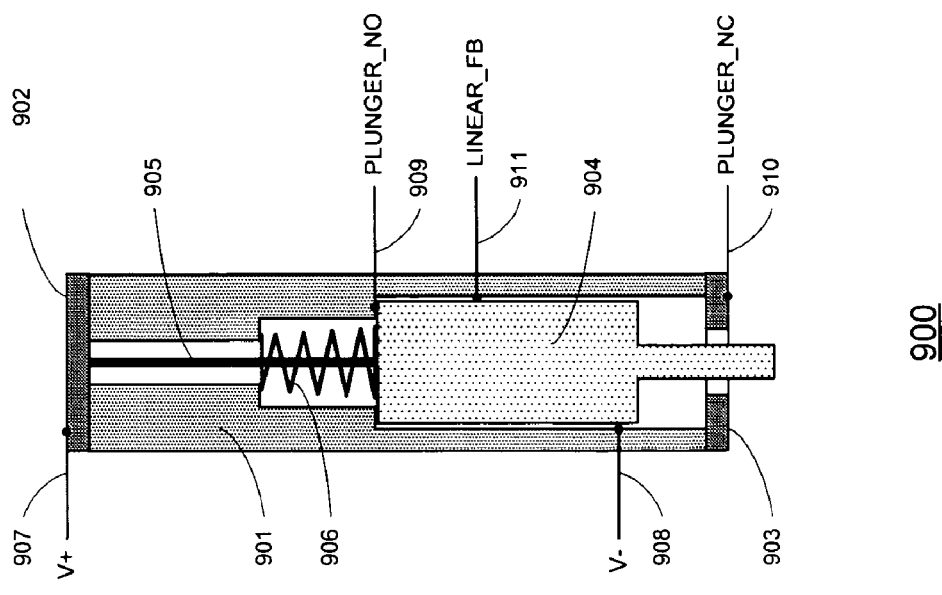
FIGS. 9A and 9B illustrate pump 900 at various stages of operation.
Figure 9A:
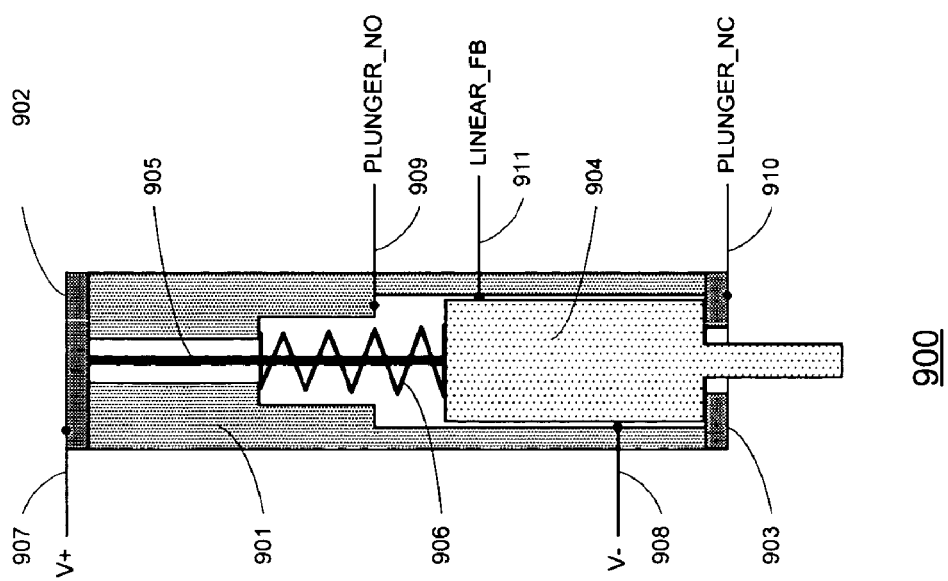

FIGS. 9A and 9B illustrate pump 900, another embodiment of the present invention. Pump 900 is similar to pump 700 but employs direct linear feedback in addition to the feedback provided by the switches. This feedback is contained in a linear feedback signal ("LINEAR_FB") 911 shown in the figures. Linear feedback may also be used to detect priming of the pump, which will be described later with regard to FIG. 11.

Figure 9C:
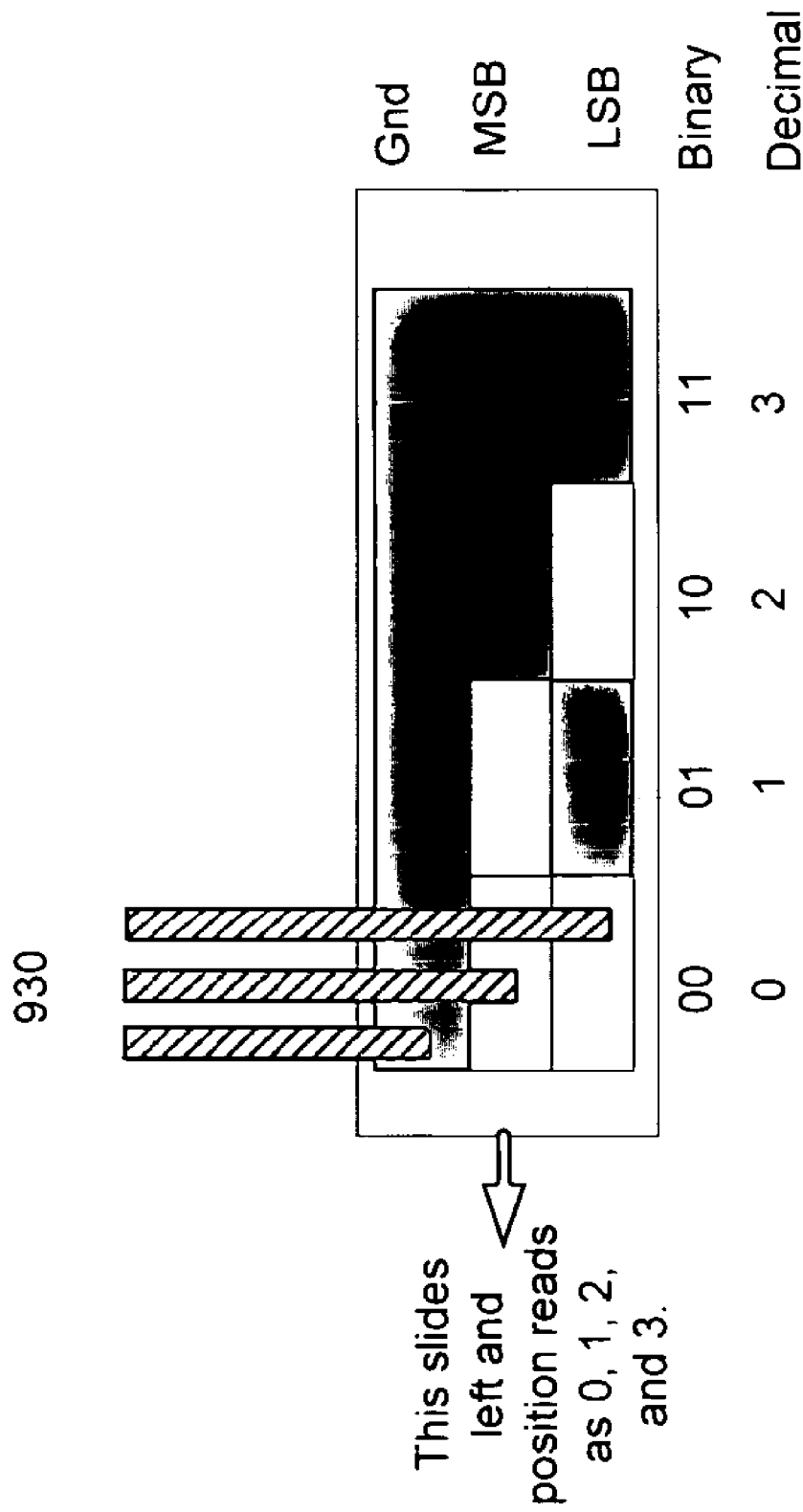
FIGS. 9C, 9D, and 9E illustrate different embodiments of position encoding utilized for linear feedback.

FIG. 9C illustrates one possible embodiment of position encoding, one way of providing linear feedback. In this embodiment the encoding scheme utilizes conductive encoding marks. One way to create the encoding grid is with insulating paint silk-screened onto a conductive surface so as to insulate certain areas. This conductive coating would be on the side of the moving part. For example, it could be directly on the piston or on an attachment to the piston. The black areas of the grid are the metal surface without paint on top of them. The white areas of the grid are covered with the insulating paint. The black row (long conducting strip) at the top is a reference ground. When contacts 930 touch the black squares then they are shorted to ground. When shorted to ground they are said to form a "1" whereas when they are not they form a "0." This logic can be inverted if desired.

In the position depicted in FIG. 9C, the ground contact is insulated from the most significant bit ("MSB") contact and the least significant bit ("LSB") contact. Therefore it is at position 0 (binary position 00). As this moving part slides left under the contacts 930, then position 1 (binary position 01) will next be sensed. When the part slides left again position 2 (binary position 10) will next be sensed etc. . . . FIG. 9C illustrates 4 positions, that is 2 bits of encoding for illustrative purposes. However, this can be extended to any number of positions. For example, 32 positions would require 5 bits. This digital position sensing can be used for digital feedback and control of the piston, and thus can be used to control position of the piston and the amount of insulin delivered.

Optical encoding may be employed instead of the conductive encoding described above. Instead of shorted contacts, an optical sensor (an LED+photocell, for example) is used to sense if the shiny metal is present or if light absorbing black paint is present.

Figure 9D:
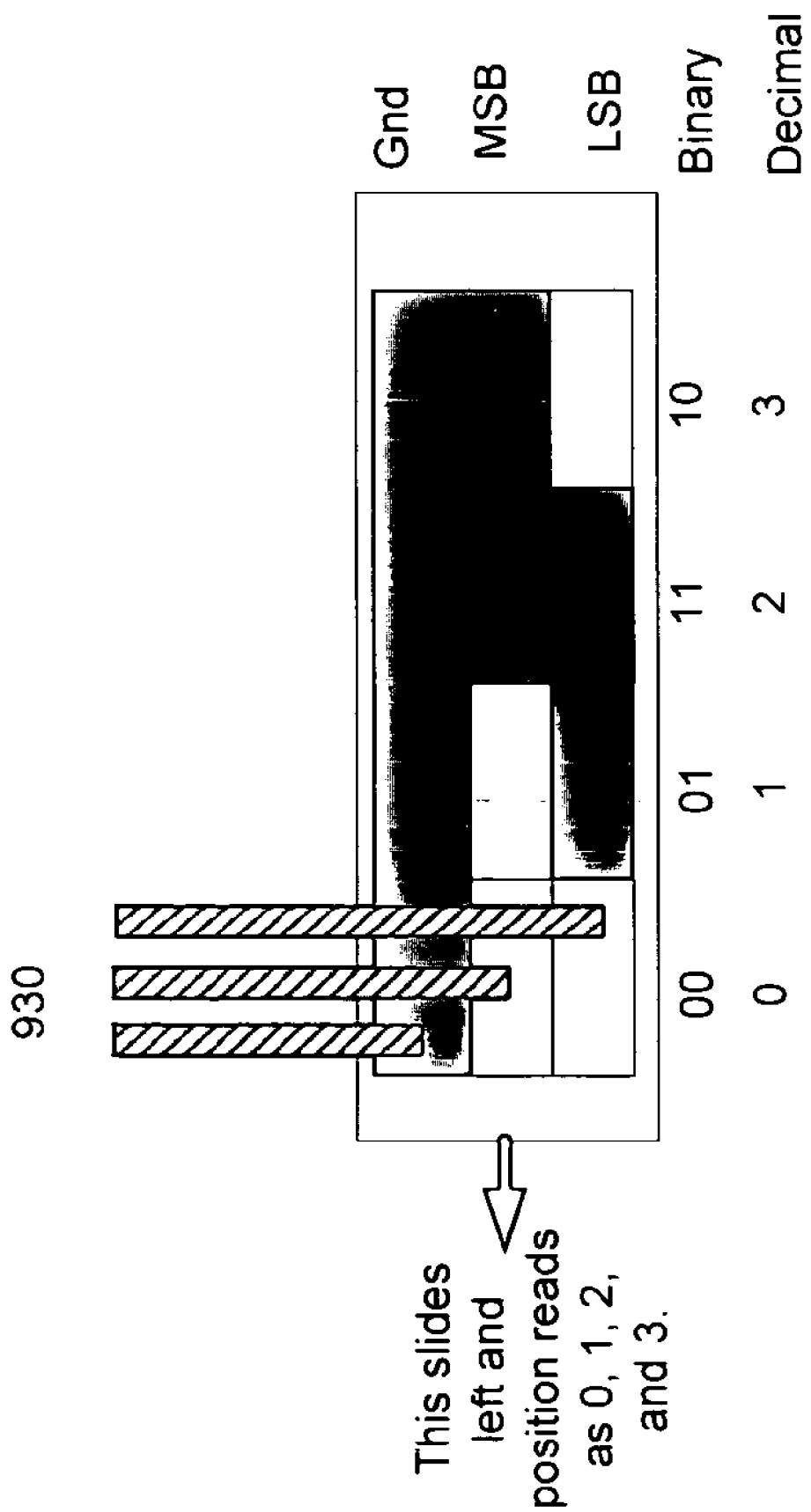

A minor modification to the encoding shown in FIG. 9C is shown in FIG. 9D. In FIG. 9D the encoding marks or bits are laid down in a Grey code. That is, only one bit change is allowed per position. Grey codes have several desirable properties that are well known in the art.

Degradation of the contacts and various other parts can occur over time. For example, contacts can be dirty, worn, or broken, and contamination may cause faulty contact readings, etc. This would normally cause an error or misread. There are various ways to minimize the errors and to correct any errors that may occur. In one method, additional bits are added to the surface. A single bit (called a parity bit) can be added to detect some kinds of errors. Multiple bits can be added for even more error protection. With several added bits errors can be both detected and corrected. A measure of this is the Hamming distance, which is well known in the art. Briefly stated, the Hamming distance can be interpreted as the number of bits which need to be changed to turn one string into the other. Sometimes the number of characters is used instead of the number of bits.

Figure 9E:
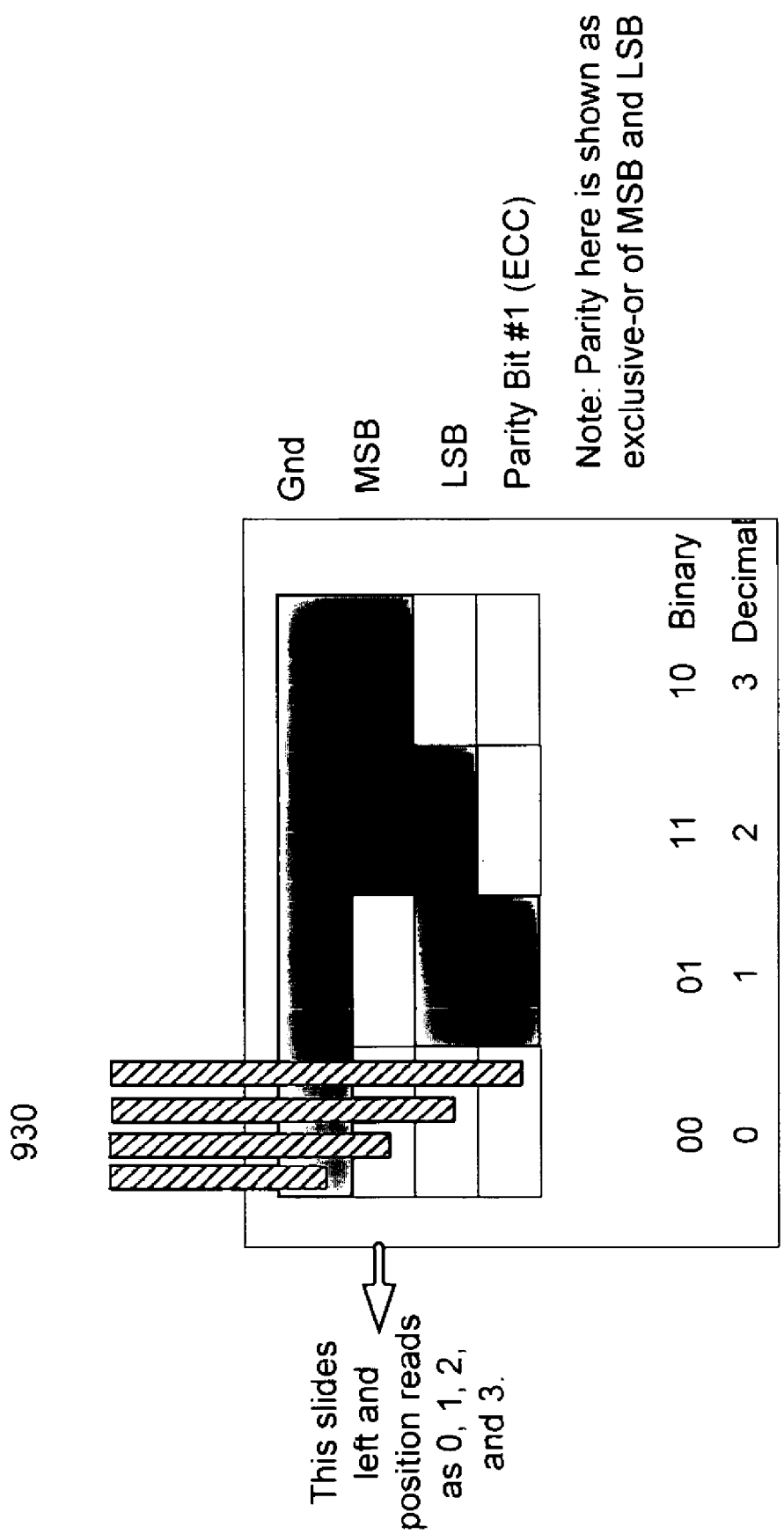
Figure 10:
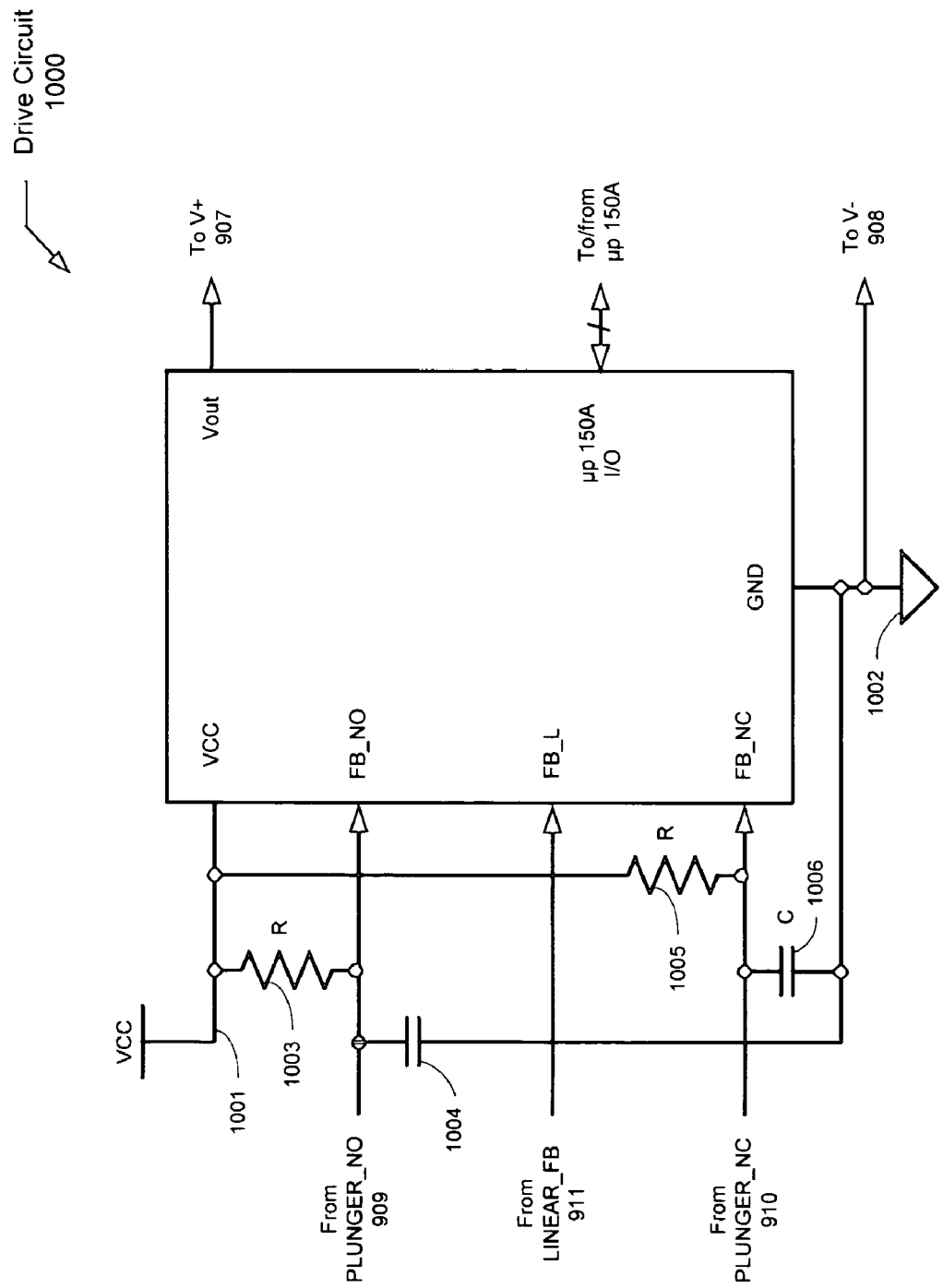
FIG. 10 illustrates an embodiment of a pump drive circuit for use with pump 900 or other pump embodiments.

Error detection and correction theory is a well known science used as a part of radio communications theory, and can be applied to the encoding and position recognition mechanisms of the present invention. This includes BCH codes, parity codes, and Reed-Solomon codes, etc. The system of FIG. 9E includes a parity bit that can be used for error correction encoded on the moving object.

Analog sensing of position can be made by plating two plastic, insulated surfaces with metal, or alternatively simply providing two metal surfaces. The two surfaces are used as capacitor plates—and together form a capacitor. One capacitor plate would be stationary, while the other capacitor plate would be part of the moving assembly including the piston. The measured capacitance is proportional to the distance between the plates, and therefore can be used to measure the position of the piston. This analog position sensing can be used for feedback and control of the moving part.

Analog sensing of position can also be achieved with magnetic measurements by adding a magnet to the moving part and sensing on the stationary part. Similar to the capacitance measurement described above, the magnetic field will vary depending on the distance between the moving and stationary parts. Therefore, the magnetic sensor may be used to measure the position of the piston and this type of analog position sensing can be used for feedback and control of the moving part. One type of well known magnetic sensor is a Hall Effect sensor, but any magnetic sensor may be utilized.

Resistance measurements may be used to implement analog linear feedback. Similar to a potentiometer, the piston will have different resistance values the further a measurement is taken along the length of the plunger. In other words, the resistance will increase with distance a current must travel.

Usage of the linear feedback has many advantages. One advantage of employing the feedback is that the drive circuit can "servo" the plunger or control the position or stroke of the plunger with a relatively high degree of accuracy. Thus, a partial plunger stroke may be used to give finer dose delivery, and that dose can be any fraction of the pump cylinder volume. By measuring and controlling the plunger movement variable size rather than only discrete volume doses may be administered. Additionally, a partial plunger stroke may not only be detected when it is undesirable (as in pump 700), but the volume of the partial stroke may be measured and compared to the expected volume thus adding fault resolution. For instance, if a full stroke was supposed to take place and deliver a certain volume, the system can detect that less than the desired volume was pumped and make up for the missing volume or indicate a failure condition with a measure of the error being reported. A pump having position detection and control is more fault tolerant than a pump without it. For example, if a certain portion of the full stroke range is unavailable for some reason, the pump can control the stroke to only use the available range. This could provide invaluable additional operating time in what would otherwise be a malfunctioning or inoperative pump. For a diabetic who must have insulin the value of this is potentially life-saving.

Priming, Fault Tolerance, and Servo Control

Figure 11A:
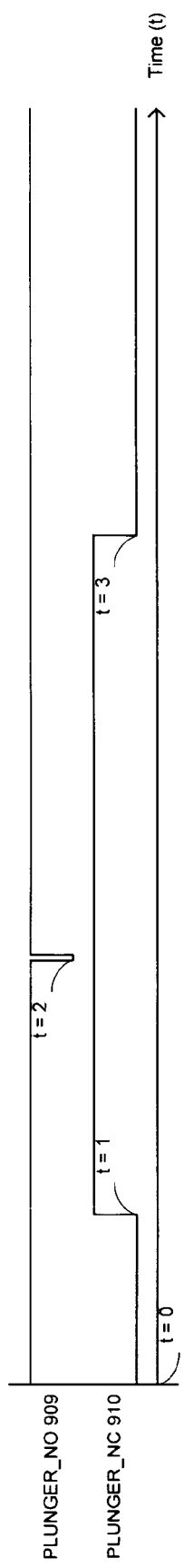
FIG. 11A is a graph of a pump operating in an unprimed state.

Another improvement to the basic pump design is to monitor the feedback as an indication of the operation of the entire pump system and not just the proper functioning of the plunger. FIG. 11A shows a pump prior to being "primed" where there is air in the pump system leading to the patient including the tubing and infusion set (the portion attached to the user where insulin is delivered to the user's tissue).

Using pump 900 as an example, although application in other embodiments such as pump 700 is also possible, at time t=0 (the initial time reference) the pump 900 is activated (the V− 908 switch is enabled if present and power is applied to the V+ 907 contact by the drive circuit 1000) as is shown in FIG. 9A. At time t=1 the plunger 904 begins to move and PLUNGER_NC 910 changes state from a Logic '0' to a Logic '1' to indicate plunger 904 movement. At time t=2 the plunger 904 activates the PLUNGER_NO 909 contact which changes state from a Logic '1' to a Logic '0' to indicate the plunger 904 has achieved a full upward stroke as is shown in FIG. 9B. This causes power to be removed by the drive circuit 1000 via the feedback (FB_NO) and shortly thereafter the plunger begins to fall and the PLUNGER_NO 909 contact changes state from a Logic '0' to back to a Logic '1' as affirmed by the drive circuit 1000 feedback. At time t=3 the plunger 904 has completed a full pump cycle and PLUNGER_NC 910 changes state back from a Logic '1' to a Logic '0' to indicate the completion of a full pump cycle as shown again in FIG. 9A (at this time the V− 908 series power switch is disabled if present to prevent possible pump "misfires" due to noise or other system errors). The digital feedback provides a simple and clear indication of a fault.

Figure 11B:
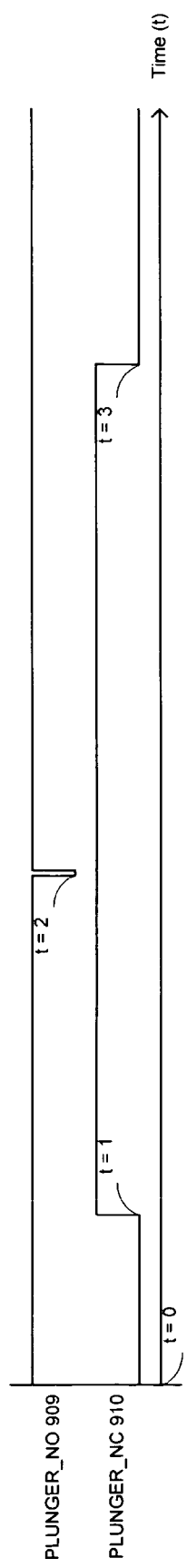
FIG. 11B is a graph of a pump operating in a primed state.

The same cycle is shown in FIG. 11B where the pump system is fully primed and operating as compared to the unprimed state shown in FIG. 11A. The time from t=1 to t=2 is shorter in FIG. 11A than in FIG. 11B as the pump 900, specifically the plunger 904, is pulling air from the reservoir versus insulin. This may be due to the initial priming where air is being purged from the system or due to a reservoir failure. Similarly the time from t=2 to t=3 is shorter in FIG. 11A than in FIG. 11B as the pump 900, specifically the plunger 904, is pushing air through the tubing and infusion set versus insulin. In fact, the time from t=2 to t=3 may be used to detect a fully primed pump that is ready for insertion. If the tubing or infusion set were to break after insertion than the time from t=2 to t=3 would decrease and a fault could be detected. This phenomenon is similar to the affect of having air in brake hydraulic lines on an automobile where the brake feels soft due to the compressibility of air versus fluid. Priming the pump is analogous to "bleeding" the brakes. When the pump is primed it takes more energy to push the fluid through the tubing and infusion set. This pressure may increase even more when the insulin is pushed into the user's body (tissue). Since the plunger 904 is driven by the plunger spring 906, the extra force becomes related to time and is measured as the time from t=2 to t=3.

In fact, the priming techniques described above may be used to automatically prime a pump under the control of the microprocessor 150A. Rather than have the user prime the pump manually, and stop when fluid, such as insulin, begins to emerge from the tip of an infusion set (not shown), the pump can use the feedback described above to prime the pump automatically and optionally ask the user to confirm that priming is complete. The priming can include the entire infusion set or other attachment to the pump, and not just the pump itself. This enhancement is especially important for young pump users and those who are vision impaired or otherwise have poor eyesight. Those users can rely on the automatic priming and can (optionally) confirm the priming by feeling the liquid as it exits the final point to be primed.

This automatic priming technique also applies in a similar fashion to other pump systems. For example, on a syringe pump system with a stepper motor, the power to the motor when monitored is an indication of the work done by the motor in a fashion analogous to work done by the plunger spring 906. The work would be monitored by a shunt resistor used to measure the motor current, or alternatively the droop in the battery or power supply would be monitored to indicate power used by the motor and thus work done by the pump.

Figure 11C:
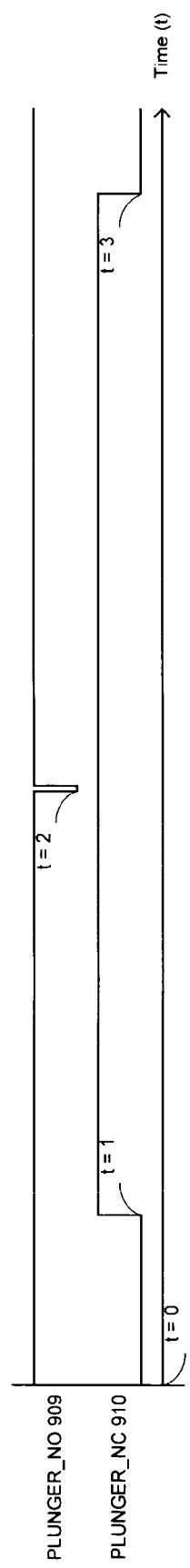
FIG. 11C is a graph of occlusion detection within a pump.

FIG. 11C illustrates the occurrence and detection of an input occlusion (increase in time from t=1 to t=2) and output occlusion (increase in time from t=2 to t=3). This system preferably accounts for circuit variation and battery voltage droops so that these conditions are erroneously interpreted as an input or output occlusion.

The actuation of the plunger or piston can be modified or servo controlled to make the pump operate more efficiently and to reduce stress on the pump. This would allow for a smaller and lighter pump with improved reliability.

Figure 12A:
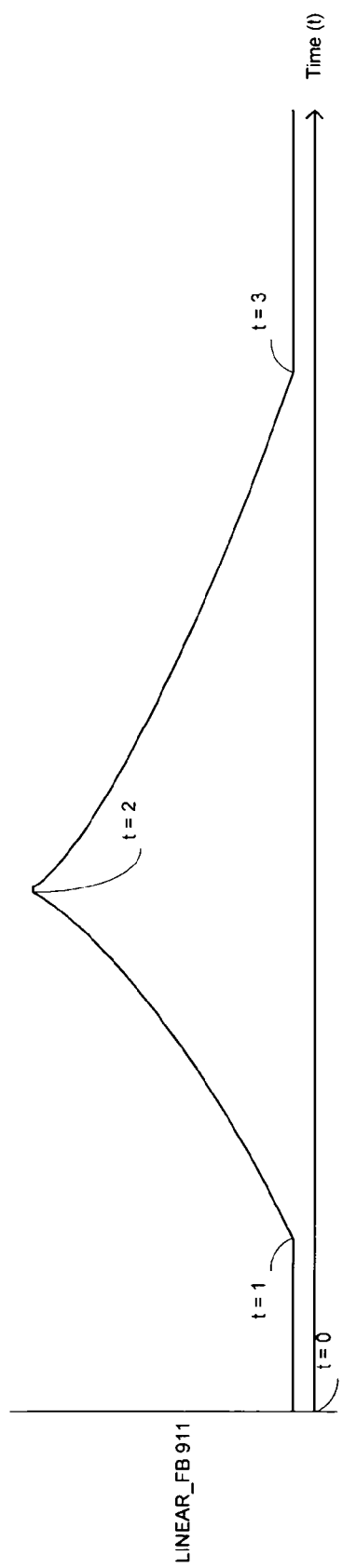
FIGS. 12A and 12B are graphs of pump operation over time.

FIG. 12A is a graph illustrating pumping operation over time. The times in FIG. 12A correspond to the times shown in FIG. 11B. The rate of change of the position, as indicated by linear feedback signal 911 increases over time until the piston reaches the top of its travel at time t=2. This will result in significant stress when the piston hits the hard stop.

Figure 12B:
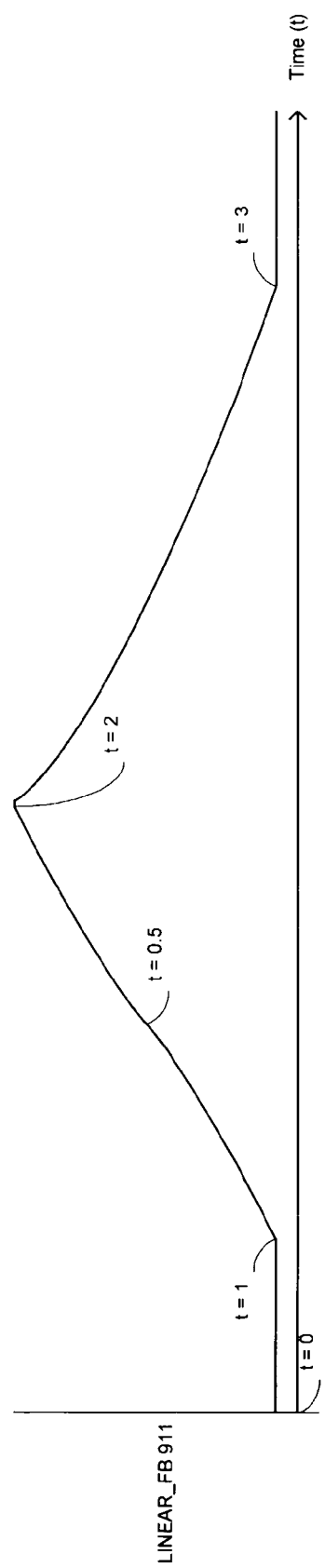

FIG. 12B is a graph illustrating pumping operation over time where the piston movement is modulated to reduce the acceleration and velocity of the piston before it hits the hard stop. This will reduce the amount of stress encountered by all of the moving parts of the pump. At time t=0.5 the power from the drive circuit 1000 is reduced to reduce the stress (impact) at time t=2. This can include pulse width modulation ("PWM") of the potential applied to the shape memory element. For example, the PWM rate may be modified to a new value or changed per a specified profile. Similar modification to the action of the piston could modify the profile leading to t=3 by adding occasional small pulses of energy to slow the descent of the plunger 904.

Although the various aspects of the present invention have been described with respect to exemplary embodiments thereof, it will be understood that the present invention is entitled to protection within the full scope of the appended claims.

It is claimed:

1. A pumping system comprising:
a chamber;
a piston within the chamber;
a shape memory element within the chamber that changes length when a current flows through the shape memory element,
the shape memory element moving the piston between a first physical limit at a proximal end of the chamber and second physical limit at a distal end of the chamber, such that when the piston is at the first physical limit the chamber is filled with fluid and when the piston is at the second physical limit the chamber is discharged of fluid;
a first switch at the first physical limit that indicates the piston is in contact with the first physical limit; and
a processor programmed to measure a first time period, wherein the first time period is the time it takes for the piston to move between the proximal end and the distal end, to compare the first time period to a predetermined time period, and to determine that the pumping system is not primed when the first time period is below the predetermined time period by a threshold amount of time.

2. The pumping system of claim 1 further comprising circuitry that senses a condition of the first switch.

3. The pumping system of claim 2, wherein the circuitry is operable to detect a malfunction when the piston is not at the first physical limit.

4. The pumping system of claim 3, wherein the circuitry is operable to terminate activation of the piston when the malfunction is detected.

5. The pumping system of claim 2, wherein the circuitry is operable to terminate activation of the piston when the piston is at the first physical limit.

6. The pumping system of claim 5, wherein terminating activation of the piston comprises discontinuing the current through the shape memory element.

7. The pumping system of claim 1, wherein the first physical limit comprises a conductive material.

8. A method for pumping a fluid from a pump, the method comprising:
moving a piston in a chamber between a first physical limit at a proximal end of the chamber and a second physical limit at a distal end of the chamber, wherein the piston is moved from the first physical limit to the second physical limit by a shape memory element that expands and contracts when a pulse is applied to the shape memory element;
drawing fluid into the chamber when the piston moves towards the first physical limit;
expelling fluid from the chamber when the piston moves towards the second physical limit;
detecting, using a switch disposed at the first physical limit, when the piston is in contact with the first physical limit;
measuring a first time period, wherein the first time period is the time it takes for the piston to move between the proximal end and the distal end;
comparing the first time period to a predetermined time period; and
determining that the pump is not primed when the first time period is below the predetermined time period by a threshold amount of time.

9. The method of claim 8, further comprising detecting the condition of the switch.

10. The method of claim 8, further comprising detecting a malfunction when the piston does not reach the first physical limit.

11. The method of claim 10, further comprising discontinuing the pulse to the shape memory element when the malfunction is detected.

12. The method of claim 8, further comprising discontinuing the pulse to the shape memory element when the piston reaches the switch at the first physical limit.

13. A pump comprising:
a chamber having at least a first physical limit at a proximal end of the chamber and a second physical limit at a distal end of the chamber;
a first piston disposed within the chamber;
a shape memory element coupled to the first piston, wherein the shape memory element is configured to move between an extended state and a contracted state when a current is applied thereto, wherein when the shape memory element moves between the extended state and the contracted state, the first piston moves from the first physical limit to the second physical limit;

at least one switch disposed on at least one of the first physical limit and the second physical limit, wherein the at least one switch indicates when the first piston is in contact with the at least one of the first physical limit or the second physical limit; and a processor programmed to measure a first time period, wherein the first time period is the time it takes for the piston to move between the proximal end and the distal end, to compare the first time period to a predetermined time period, and to determine that the pump is not primed when the first time period is below the predetermined time period by a threshold amount of time.

14. The pump of claim 13, further comprising circuitry configured to detect a condition of the at least one switch.

15. The pump of claim 14, wherein the circuitry is configured to detect a malfunction of the pump.

16. The pump of claim 15, wherein the circuitry is configured to discontinue operation of the pump when the malfunction is detected.

17. The pump of claim 13, wherein at least one of the first physical limit and the second physical limit is comprised of conductive material.

* * * * *

UNITED STATES PATENT AND TRADEMARK OFFICE
CERTIFICATE OF CORRECTION

| | | |
|---|---|---|
| PATENT NO. | : 8,047,811 B2 | Page 1 of 1 |
| APPLICATION NO. | : 12/345545 | |
| DATED | : November 1, 2011 | |
| INVENTOR(S) | : Benjamin M. Rush et al. | |

It is certified that error appears in the above-identified patent and that said Letters Patent is hereby corrected as shown below:

Column 6, line 62, replace "piston 209" with --piston 206--
    Column 7, line 31, replace "top cap 607" with --top cap 602--
    Column 7, line 34, replace "pump 600" with --pump 400--

Signed and Sealed this
Twenty-first Day of February, 2012

David J. Kappos
*Director of the United States Patent and Trademark Office*